(12) United States Patent
Mihashi et al.

(10) Patent No.: US 7,216,980 B2
(45) Date of Patent: *May 15, 2007

(54) EYE CHARACTERISTIC MEASURING APPARATUS

(75) Inventors: Toshifumi Mihashi, Tokyo (JP); Yoko Hirohara, Tokyo (JP)

(73) Assignee: Kabushiki Kaisha Topcon, Tokyo (JP)

(*) Notice: Subject to any disclaimer, the term of this patent is extended or adjusted under 35 U.S.C. 154(b) by 628 days.

This patent is subject to a terminal disclaimer.

(21) Appl. No.: 10/470,737

(22) PCT Filed: Feb. 8, 2002

(86) PCT No.: PCT/JP02/01096

§ 371 (c)(1),
(2), (4) Date: Aug. 8, 2003

(87) PCT Pub. No.: WO02/064030

PCT Pub. Date: Aug. 22, 2002

(65) Prior Publication Data

US 2004/0070730 A1  Apr. 15, 2004

(30) Foreign Application Priority Data

Feb. 9, 2001   (JP) ............................. 2001-033945
Apr. 18, 2001  (JP) ............................. 2001-119145
Apr. 18, 2001  (JP) ............................. 2001-120002

(51) Int. Cl.
*A61B 3/10* (2006.01)

(52) U.S. Cl. ...................... 351/205; 351/211; 351/212; 351/221

(58) Field of Classification Search ................ 351/205, 351/208, 209, 211, 212, 247, 206, 221
See application file for complete search history.

(56) References Cited

U.S. PATENT DOCUMENTS 4,859,051 A   8/1989   Fukuma et al.

(Continued)

FOREIGN PATENT DOCUMENTS

JP   5-75412 B2   10/1993

(Continued)

*Primary Examiner*—Huy K. Mai
(74) *Attorney, Agent, or Firm*—Foley & Lardner LLP

(57) ABSTRACT

The aberration and refraction power data of an eye to be examined obtained from a first light reception unit and cornea data of the eye to be examined are correlated with each other so as to be overlaid accurately. A first signal and a second signal are concurrently captured, and the optical characteristics and cornea shape of the eye to be examined are measured concurrently or almost concurrently. A measuring unit (111) measures dioptrical characteristics based on a first light reception signal from the first light reception unit (23), and measures a corneal topography based on a second light reception signal from the second light reception unit (35). A coordinates setting unit (112) converts signal in first and second coordinate systems, corresponding to the eye to be examined, included in the first and second reception signal into signal in reference coordinate systems respectively. A conversion unit (116) synthesizes the first and second optical characteristics of the eye to be examined obtained by the measuring unit (111) in association with each reference coordinate system formed by the coordinates setting unit (112). A measuring timing determining unit (117) determines the measuring timing of the first signal and the second signal to be subjected to measuring operation based on the first and/or second signal.

36 Claims, 22 Drawing Sheets

U.S. PATENT DOCUMENTS

| | | | | |
|---|---|---|---|---|
| 5,909,270 A | * | 6/1999 | Moser et al. | ............ 351/212 |
| 6,234,978 B1 | | 5/2001 | Mihashi et al. | |
| 6,685,320 B2 | * | 2/2004 | Hirohara et al. | ............ 351/221 |

FOREIGN PATENT DOCUMENTS

| | | |
|---|---|---|
| JP | 7-136120 A | 5/1995 |
| JP | 8-052112 A | 2/1996 |
| JP | 2612263 B2 | 2/1997 |
| JP | 9-201334 A | 8/1997 |
| JP | 10-033483 A | 2/1998 |
| JP | 10-305013 A | 11/1998 |
| JP | 2942312 B2 | 6/1999 |
| JP | 2000-237135 A | 9/2000 |
| JP | 2000-254099 A | 9/2000 |
| JP | 2000-262468 A | 9/2000 |
| JP | 2000-287930 A | 10/2000 |

* cited by examiner

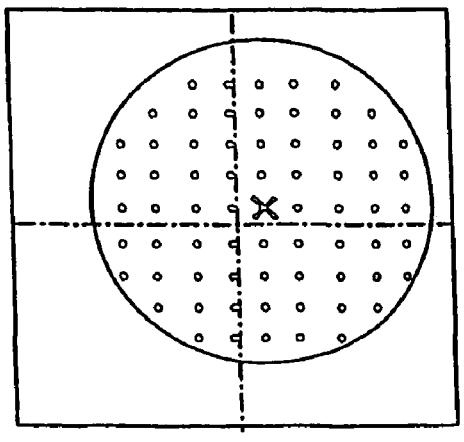
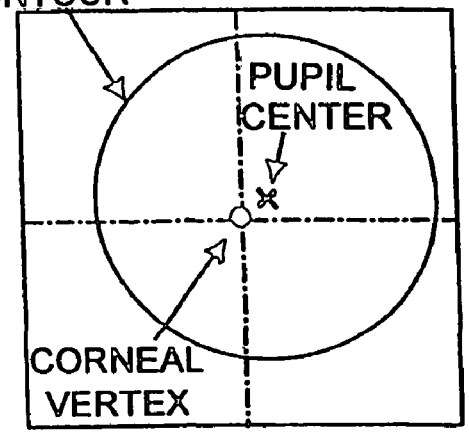
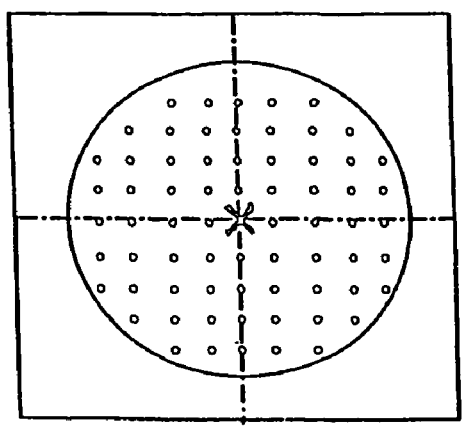
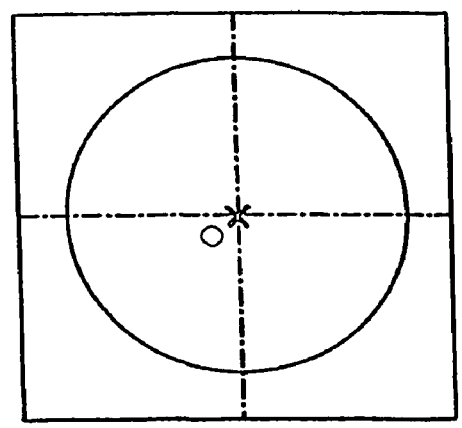
FIG. 6(A)  FIG. 6(B)

CORNEAL HIGHER ORDER
ABERRATION MAP

OCULAR HIGHER ORDER
ABERRATION MAP

DIFFERENTIAL HIGHER ORDER
ABERRATION MAP

INTERNAL ABERRATIONS

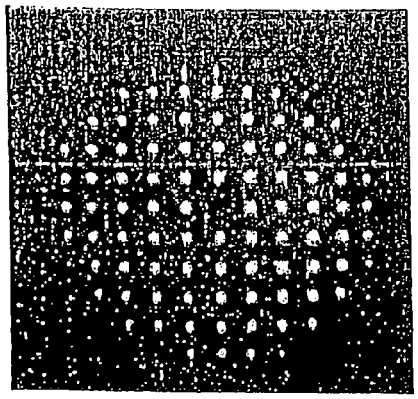
FIG. 9(A)
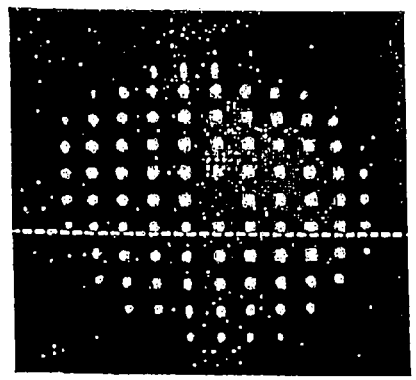
FIG. 9(B)
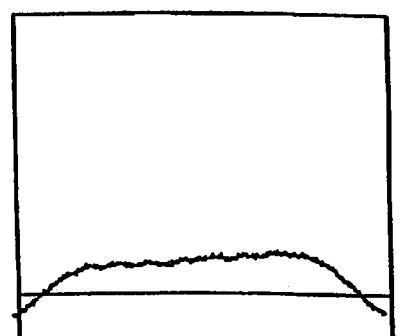
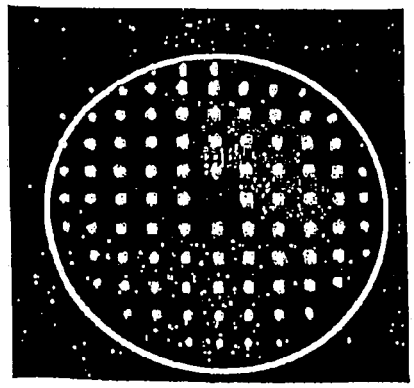
FIG. 9(C)

TABLE SHOWING ELEMENTS WHICH CAN BE DETECTED BY FIRST SIGNAL AND SECOND SIGNAL

|  | BLINK | TEAR FILM | PUPIL DIAMETER | EYELID OPENING | FIXATION STATE |
|---|---|---|---|---|---|
| FIRST SIGNAL | ○ | ○ | ○ | △ | × |
| SECOND SIGNAL | ◎ | ◎ | ◎ | ◎ | ○ |

NOTE: ○··· POSSIBLE   ◎··· GOOD   ×··· IMPOSSIBLE   271

TABLE SHOWING FITTING CONDITIONS IN A CASE WHERE SAME ELEMENT IS DETECTED BY DIFFERENT SIGNALS   272

| FIRST * SECOND SIGNALS | ◎ | ◎ | ◎ | ◎ | — |
|---|---|---|---|---|---|

TABLE SHOWING FITTING CONDITIONS IN A CASE WHERE DIFFERENT ELEMENTS OR SAME ELEMENT IS DETECTED BY DIFFERENT SIGNALS

| | | SECOND SIGNAL | | | | |
|---|---|---|---|---|---|---|
| | | BLINK | TEAR FILM | PUPIL DIAMETER | EYELID OPENING | FIXATION STATE |
| FIRST SIGNAL | INTERNAL ABNORMALITY | ○ | ○ | ○ | ○ | ○ |
| | BLINK | ◎ | ○ | ○ | ○ | ○ |
| | TEAR FILM | ○ | ◎ | ○ | ○ | ○ |
| | PUPIL DIAMETER | ○ | ○ | ◎ | ○ | ○ |
| | EYELID OPENING | ○ | ○ | ○ | ◎ | ○ |
| | FIXATION STATE | — | — | — | — | — |

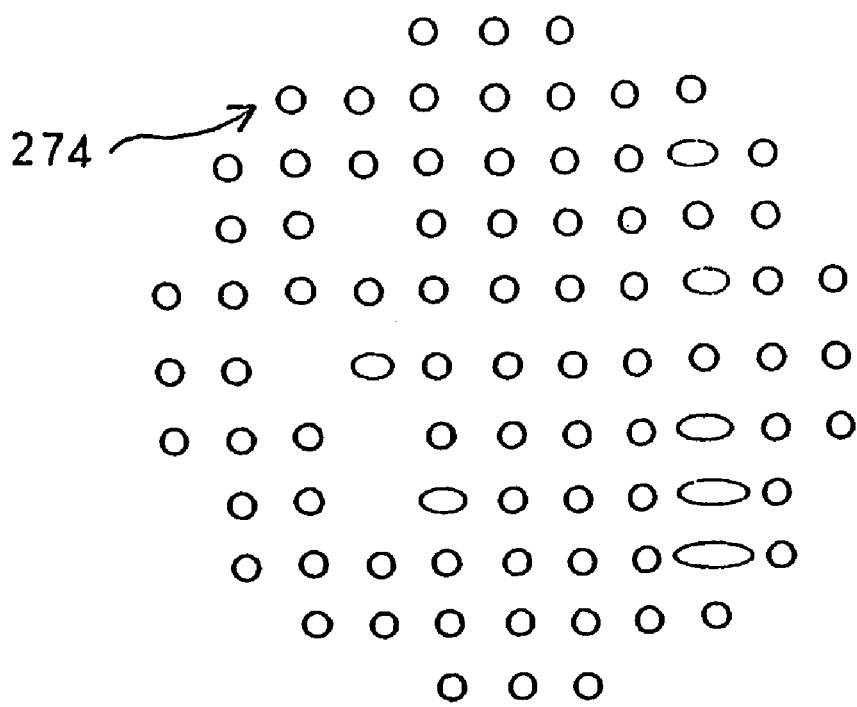
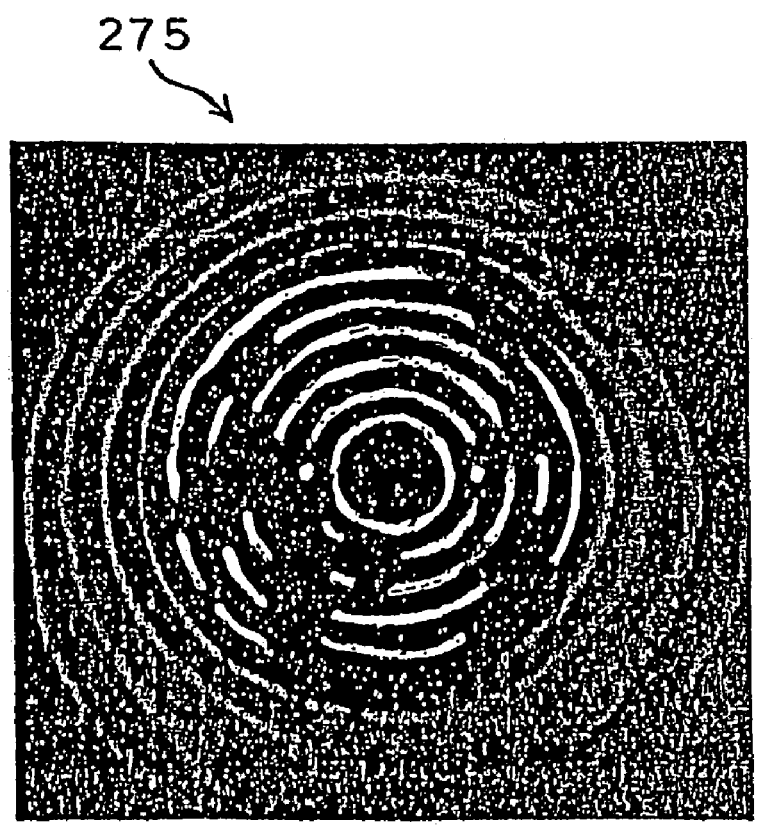
FIG. 14

EYE CHARACTERISTIC MEASURING APPARATUS

TECHNICAL FIELD

The present invention relates to an eye characteristic measuring apparatus. Particularly, the invention relates to an eye characteristic measuring apparatus which measures an optical characteristic of an eye, and correlates this with a specified coordinate system of a subject eye, a measuring apparatus or a surgical apparatus, and displays it. Besides, the invention particularly relates to an eye characteristic measuring apparatus which decides measuring timings of the optical characteristic of the subject eye and the corneal shape, and measures these simultaneously or substantially simultaneously.

BACKGROUND ART

In recent years, an optical equipment used for medicine has been developed variously to a high degree. Especially in ophthalmology, the optical equipment becomes widespread as an optical characteristic measuring apparatus for testing an eye function, such as refraction of an eye or adjustment thereof, and the inside of an eye. In the measurement results of these various tests, it becomes important that for example, a patient's eye to be measured as a test object is put in what decision factor for measuring timing.

Besides, in general, corneal topography is effective in many uses, for example, prediction of results of a surgical operation such as keratotomy or keratectomy, clinic after corneal transplant, design and evaluation of contact lenses for shortsightedness or farsightedness, diagnosis of a cornea and judgment of a disease thereof, and the like. As a conventional measuring method of a corneal shape, there is, for example, a Placido disk technique, a stereoscopic photography technique, a moire technique, a topography interference technique or the like.

As the optical characteristic measuring apparatus, for example, there is known an apparatus in which a point light source is projected on a retina and is converted into a predetermined number of beams by a conversion member such as a Hartmann plate, and the beams are received by a light receiving part to measure the optical characteristic of the eye, or a corneal shape measuring apparatus in which a Placido's disk with visible light is used to measure the corneal shape. Incidentally, in the present specification, a signal obtained through a Hartmann plate required for measuring an optical characteristic of an eye to be measured is made a first signal, and a signal obtained through a Placido's disk required for measuring a corneal shape of the eye to be measured is made a second signal.

However, in the conventional eye characteristic measuring apparatus, a processing has been performed such that a coordinate of the measuring apparatus itself, for example, the center of a light receiving part is made the origin of coordinates. Thus, according to such a coordinate system, for example, in a surgical apparatus, there is a case where measurement data is not fully related to the eye, and it is not necessarily suitable. Besides, as a conventional measuring apparatus, there is an apparatus called a photo-refract meter for obtaining the refractive power of a subject eye and a corneal shape, however, a display is not necessarily carried out in the same coordinate system.

In general, at a point of time when an alignment is adjusted manually or automatically, a measurement is started manually or automatically, however, a coordinate system (CCD coordinate) attached to a CCD at the time of the measurement corresponds to a CCD coordinate of an object side (eye side) opposite to the CCD through a lens. Although a measurement with a Hartmann wavefront sensor (first measurement system) and a corneal shape measurement (second measurement system) are substantially simultaneously performed in the respective CCDs, there is a case where the measurements are performed at times which are not identical strictly. Thus, for example, the eye is moved in the measurement, which becomes a main cause, and there is no guarantee that the CCD coordinate system of the first measurement system becomes identical to the CCD coordinate of the second measurement system. Besides, it is already performed to obtain a pupil edge from an anterior eye image and to use it for alignment. However, in the case where the acquisition timing of a Hartmann image is not completely coincident with the acquisition timing of the alignment image of the anterior eye part, if the alignment is made by only the alignment image of the anterior eye part, there is a possibility that a deviation occurs in the alignment of the Hartmann measurement by the movement of an eye or the like.

Further, in recent years, in an orthokeratology surgical operation, there has arisen a request to superimpose optical characteristic measurement data, such as aberrations of the subject eye or refractive power data, obtained from a first light receiving part as an eye optical characteristic measurement system upon corneal topography measurement data, such as corneal data of the subject eye, obtained from a second light receiving part as a corneal topography measurement system.

Besides, in the convention optical characteristic measuring apparatus, a case is conceivable in which it is difficult to simultaneously measure the optical characteristic of the subject eye and the corneal shape.

In view of the above, an object of the invention is to provide an eye characteristic measuring apparatus which correlates the aberrations of a subject eye or refractive power data obtained from a first light receiving part with corneal data of the subject eye obtained from a second light receiving part so that they can be precisely superimposed. Besides, an object of the invention is to match coordinates of a corneal shape measurement and a wavefront measurement using the same image as an alignment system by graphically comparing pupils of both to make positions coincident with each other, or to correlate a coordinate system of the alignment system with a coordinate system of the wavefront measurement.

Further, an object of the invention is to provide a structure adequate to capture a first signal of a first measurement system and a second signal of a second measurement system simultaneously or substantially simultaneously. Besides, an object of the invention is to provide a structure adequate to continuously capture a first signal and a second signal simultaneously or substantially simultaneously. Besides, an object of the invention is to perform a measurement when a first signal and a second signal are put into a state suitable for the measurement. Besides, an object of the invention is to perform a measurement in such a state that when there are plural factors exerting influences on the measurement, highly reliable measurement results can be obtained by judging the suitability of those factors by use of signals adequate to detect them and by deciding measuring timings.

DISCLOSURE OF THE INVENTION

According to first solving means of the invention, an eye characteristic measuring apparatus comprises:

a first illuminating optical system including a first light source part for emitting a first light flux of a first wavelength, for illuminating a retina of a subject eye with the first light flux from the first light source part;

a first light receiving optical system including a first light receiving part for forming a first received light signal as a first coordinate system from a received light flux, for converting the light flux reflected and returned from the retina of the subject eye into plural beams and guiding them to the first light receiving part;

a second light receiving optical system including a second light receiving part for forming a second received light signal, as a second coordinate system, including information of an anterior eye part from a received light flux, for guiding a second light flux including the information of the anterior eye part of the subject eye to the second light receiving part;

a measurement part for obtaining a first optical characteristic of the subject eye on the basis of the first received light signal from the first light receiving part and a second optical characteristic of the subject eye on the basis of the second received light signal from the second light receiving part;

a coordinate setting part for converting signals of the first and the second coordinate systems corresponding to a pupil of the subject eye included in the first and the second received light signals into signals of reference coordinate systems, respectively; and a conversion part for correlating and combining, through the respective reference coordinate systems formed by the coordinate setting part, the first and the second optical characteristics of the subject eye obtained by the arithmetic part.

Further, according to second solving means of the invention, an eye characteristic measuring apparatus comprises:

a first light source part for emitting a first light flux of a first near-infrared wavelength;

a first illuminating optical system for illuminating a minute region on a retina of a subject eye with the light flux from the first light source part;

a first light receiving optical system for receiving a light through a first conversion member for converting a part of a first reflected light flux, which is originated from the first light flux from the first light source part and is reflected from the retina of the subject eye, into substantially at least 17 beams;

a first light receiving part for receiving a first received light flux guided by the first light receiving optical system to form a first signal;

a second light source part for emitting a second flux of a near-infrared second wavelength longer than the first wavelength of the first light flux;

a second illuminating optical system for illuminating a vicinity of a cornea of the subject eye with the second light flux from the second light source and with a specified pattern;

a second light receiving optical system for receiving a second reflected light flux which is originated from the second light flux from the second light source part and is reflected from the vicinity of the cornea of the subject eye;

a second light receiving part for receiving a second received light flux guided by the second light receiving optical system to form a second signal; and an arithmetic part for capturing the first and the second signals from the first light receiving part and the second light receiving part at a same or substantially same timing, obtaining an optical characteristic of the subject eye on the basis of the first signal from the first light receiving part, and obtaining a corneal shape of the subject eye on the basis of the second signal from the second light receiving part.

Besides, as one of the features of the invention, for example, the optical characteristic (for example, refractive power) of the subject eye is measured on the basis of the first signal from the light receiving part (or tilt angle of the light flux obtained by the first light receiving part), and the corneal shape is measured on the basis of the second signal from the second light receiving part. As another feature of the invention, for example, without miosis of the eye to be measured, the first signal and the second signal can be captured simultaneously or simultaneously continuously plural times. As another feature of the invention, for example, timings at which the first signal and the second signal are captured and which are suitable for measurement can be decided. As another feature of the invention, for example, different factors are judged using the first signal and the second signal, plural factors are judged using only the first signal or the second signal, or an important factor (for example, blink) can be judged using both the first signal and the second signal.

BRIEF DESCRIPTION OF THE DRAWINGS

FIGS. 6(A) and 6(B) are explanatory views (1) of eye characteristic measurement.

FIGS. 9(A)–9(C) are explanatory views for obtaining a pupil edge from a Hartmann image.

FIG. 13 is an explanatory view of decision factors for measuring timing with respect to a first signal and a second signal.

FIG. 14 is an explanatory view of an image received by a first and a second light receiving parts.

DESCRIPTION OF THE PREFERRED EMBODIMENTS

Hereinafter, embodiments of the invention will be described with reference to the drawings.

Figure 1:
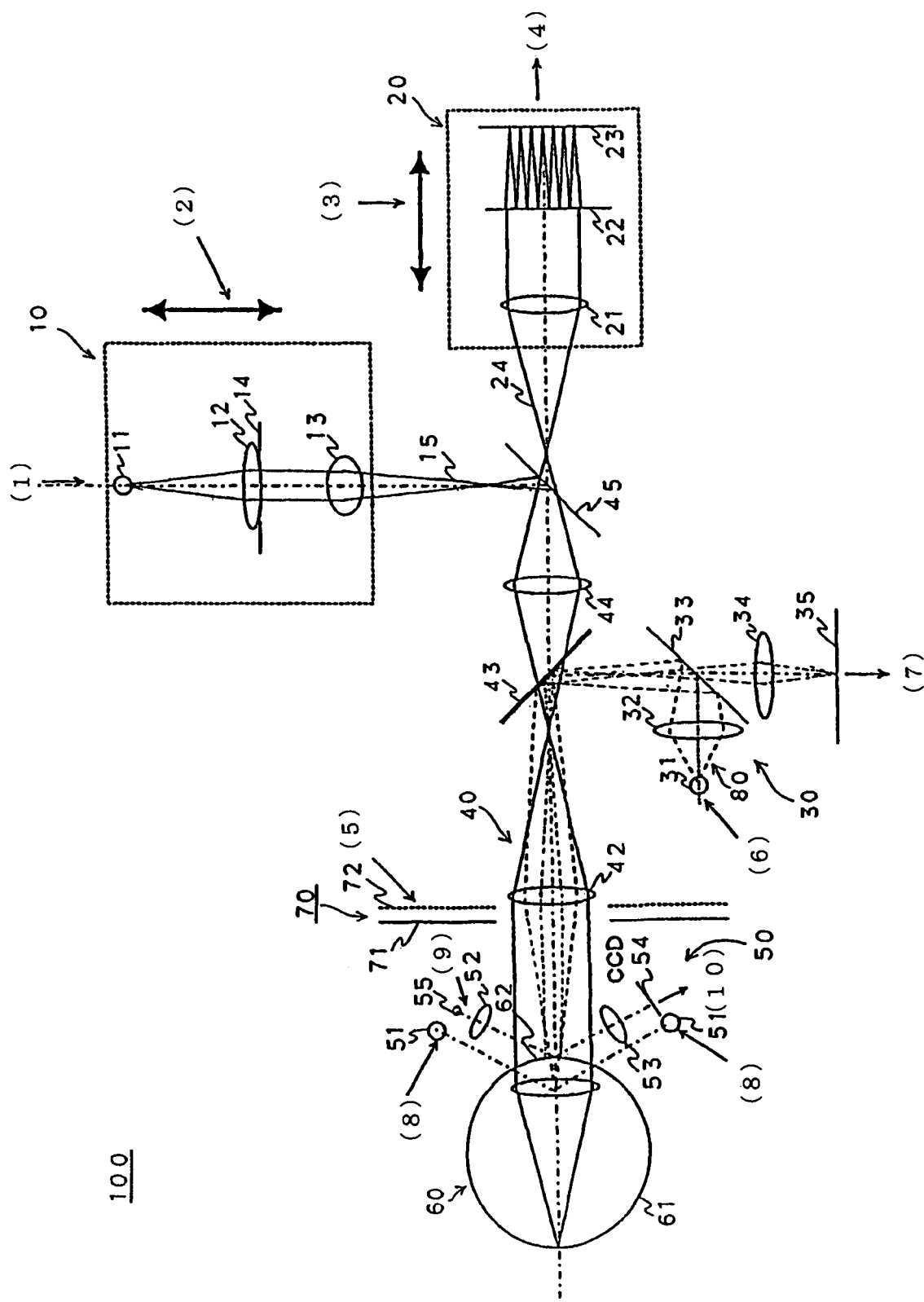
FIG. 1 is a view roughly showing an optical system 100 of an eye optical characteristic measuring apparatus of the invention.

1. Outline of an Eye Optical Characteristic Measuring Apparatus 1-1. Optical System FIG. 1 is a view roughly showing an optical system 100 of an eye optical characteristic measuring apparatus of the invention.

The optical system 100 of the eye optical characteristic measuring apparatus is an apparatus for measuring, for example, an optical characteristic of an eye 60 to be measured as an object, and includes a first illuminating optical system 10, a first light receiving optical system 20, a second light receiving optical system 30, a common optical system 40, an adjusting optical system 50, a second illuminating optical system 70, and a second light sending optical system 80. Incidentally, with respect to the eye 60 to be measured, a retina 61 and a cornea 62 are shown in the drawing.

The first illuminating optical system 10 includes, for example, a first light source part 11 for emitting a light flux of a first wavelength, and a condensing lens 12, and is for illuminating a minute region on the retina (eyeground) 61 of the eye 60 to be measured with the light flux from the first light source part 11 so that its illumination condition can be suitably set. Incidentally, here, as an example, the first wavelength of the illuminating light flux emitted from the first light source part 11 is a wavelength of an infrared range (for example, 840 nm, 780 nm, etc.).

Besides, it is desirable that the first light source part 11 has a large spatial coherence and a small temporal coherence. Here, the first light source part 11 is, for example, a super luminescence diode (SLD), and a point light source having high luminescence can be obtained. Incidentally, the first light source part 11 is not limited to the SLD, and for example, a laser having a large spatial coherence and a large temporal coherence can also be used by inserting a rotation diffused plate or the like to suitably lower the temporal coherence. Further, an LED having a small spatial coherence and a small temporal coherence can also be used, if light quantity is sufficient, by inserting, for example, a pinhole or the like at a position of a light source in an optical path.

The first light receiving optical system 20 includes, for example, a collimator lens 21, a Hartmann plate 22 as a conversion member for converting a part of a light flux (first light flux) reflected and returned from the retina 61 of the eye 60 to be measured into at least 17 beams, and a first light receiving part 23 for receiving the plural beams converted by the Hartmann plate 22, and is for guiding the first light flux to the first light receiving part 23. Besides, here, a CCD with little readout noise is adopted for the first light receiving part 23, and as the CCD, a suitable type of CCD, for example, a general low noise type of CCD, a cooling CCD of 1000*1000 elements for measurement, or the like can be applied.

Figure 2:
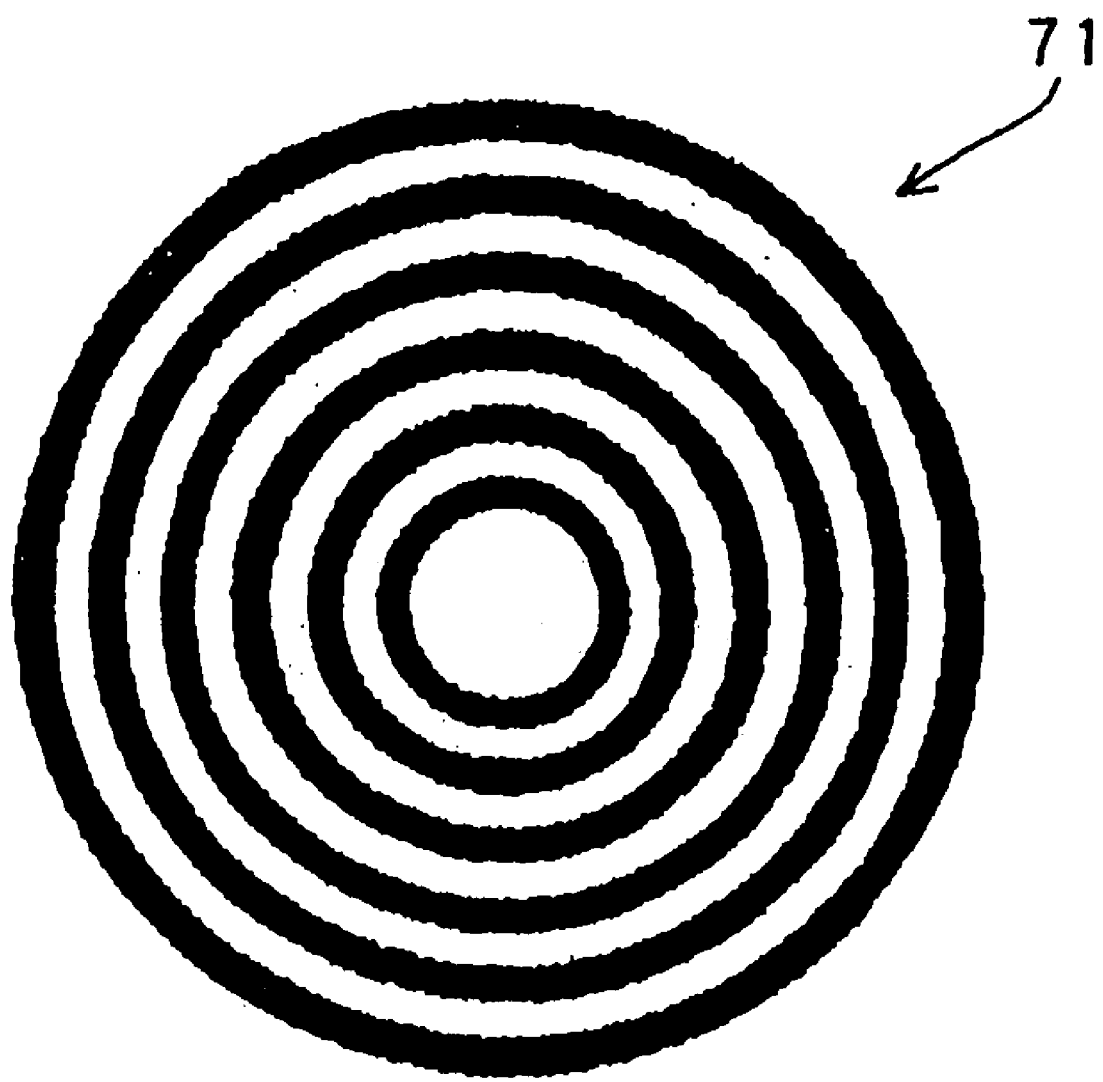
FIG. 2 is a structural view showing an example of a Placido's disk.

The second illuminating optical system 70 includes a second light source 72 and a Placido's disk 71. Incidentally, the second light source 72 can be omitted. FIG. 2 shows an example of a structural view of the Placido's disk. The Placido's disk (PLACIDO's DISK) 71 is for projecting an index of a pattern composed of plural co-axial rings. Incidentally, the index of the pattern composed of the plural co-axial rings is an example of an index of a specified pattern, and a different suitable pattern can be used. Then, after an alignment adjustment described later is completed, the index of the pattern composed of the plural co-axial rings can be projected.

The second light sending optical system 80 is for mainly performing, for example, the alignment adjustment described later, and measurement and adjustment of a coordinate origin and a coordinate axis, and includes a second light source part 31 for emitting a light flux of a second wavelength, a condensing lens 32, and a beam splitter 33.

The second light receiving optical system 30 includes a condensing lens 34 and a second light receiving part 35. The second light receiving optical system 30 guides a light flux (second light flux), which is originated from the pattern of the Placido's disk 71 illuminated from the second illuminating optical system 70 and is reflected and returned from the anterior eye part or the cornea 62 of the eye 60 to be measured, to the second light receiving part 35. Besides, it can also guide a light flux, which is emitted from the second light source part 31 and is reflected and returned from the cornea 62 of the eye 60 to be measured, to the second light receiving part 35. Incidentally, as the second wavelength of the light flux emitted from the second light source part 31, for example, a wavelength different from the first wavelength (here, 780 nm or 840 nm) and longer than that (for example, 940 nm) can be selected.

The common optical system 40 is disposed on an optical axis of the light flux emitted from the first illuminating optical system 10, can be included in the first and the second illuminating optical systems 10 and 70, the first and the second light receiving optical systems 20 and 30, the second light sending optical system 80 and the like in common, and includes, for example, an afocal lens 42, beam splitters 43 and 45, and a condensing lens 44. The beam splitter 43 is formed of such a mirror (for example, a dichroic mirror) that the wavelength of the second light source part 31 is sent (reflected) to the eye 60 to be measured, the second light flux reflected and returned from the retina 61 of the eye 60 to be measured is reflected, and the wavelength of the first light source part 11 is transmitted. The beam splitter 45 is formed of such a mirror (for example, a dichroic mirror) that the wavelength of the first light source part 11 is sent (reflected) to the eye 60 to be measured, and the first light flux reflected and returned from the retina 61 of the eye 60 to be measured is transmitted. By the beam splitters 43 and 45, the first and the second light fluxes do not mutually enter the other optical systems to generate noise.

The adjusting optical system 50 is for mainly performing, for example, a working distance adjustment described later, includes a third light source part 51, a fourth light source part 55, condensing lenses 52 and 53, and a third light receiving part 54, and is for mainly performing the working distance adjustment.

Next, the alignment adjustment will be described. The alignment adjustment is mainly carried out by the second light receiving optical system 30 and the second light sending optical system 80.

First, the light flux from the second light source part 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux such as is emitted from a point at the half of the radius of curvature of the cornea 62. The divergence light flux is received as a spot image by the second light receiving part 35 through the afocal lens 42, the beam splitters 43 and 33, and the condensing lens 34.

Here, in the case where the spot image on the second light receiving part 35 deviates from the optical axis, the main body of the eye optical characteristic measuring apparatus is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the eye 60 to be measured is illuminated by the third light source 51, and an image of the eye 60 to be measured obtained by this illumination is formed on the second light receiving part 35, and accordingly, this image may be used to make the pupil center coincide with the optical axis.

Next, the working distance adjustment will be described. The working distance adjustment is mainly carried out by the adjusting optical system 50.

First, the working distance adjustment is carried out by, for example, irradiating the eye 60 to be measured with a parallel light flux emitted from the fourth light source part 55 and close to the optical axis, and by receiving the light reflected from the eye 60 to be measured through the condensing lenses 52 and 53 by the third light receiving part 54. Besides, in the case where the eye 60 to be measured is in a suitable working distance, a spot image from the fourth light source part 55 is formed on the optical axis of the third light receiving part 54. On the other hand, in the case where the eye 60 to be measured is out of the suitable working distance, the spot image from the fourth light source part 55 is formed above or below the optical axis of the third light receiving part 54. Incidentally, since the third light receiving part 54 has only to be capable of detecting a change of a light flux position on the plane containing the fourth light source part 55, the optical axis and the third light receiving part 54, for example, a one-dimensional CCD arranged on this plane, a position sensing device (PSD) or the like can be applied.

Next, a positional relation between the first illuminating optical system 10 and the first light receiving optical system 20 will be roughly described.

The beam splitter 45 is inserted in the first light receiving optical system 20, and by this beam splitter 45, the light from the first illuminating optical system 10 is sent to the eye 60 to be measured, and the reflected light from the eye 60 to be measured is transmitted. The first light receiving part 23 included in the first light receiving optical system 20 receives the light transmitted through the Hartmann plate 22 as the conversion member and generates a received light signal.

The first light source 11 and the retina 61 of the eye 60 to be measured form a conjugated relation. The retina 61 of the eye 60 to be measured and the first light receiving part 23 are conjugate. Besides, the Hartmann plate 22 and the pupil of the eye 60 to be measured form a conjugated relation. That is, the front focal point of the afocal lens 42 is substantially coincident with the pupil of the eye 60 to be measured.

Besides, the first illuminating optical system 10 and the first light receiving optical system 20 are moved together so that a signal peak by the reflected light at the first light receiving part 23 becomes maximum on the condition that the light flux from the first light source part 11 is reflected at a point on which it is condensed. Specifically, the first illuminating optical system 10 and the first light receiving optical system 20 are moved in a direction in which the signal peak at the first light receiving part 23 becomes large, and are stopped at a position where the signal peak becomes maximum. By this, the light flux from the first light source part 11 is condensed on the eye 60 to be measured.

The lens 12 converts a diffused light of the light source 11 into a parallel light. A diaphragm 14 is positioned at an optically conjugated position with respect to the pupil of the eye or the Hartmann plate 22. The diaphragm 14 has a diameter smaller than an effective range of the Hartmann plate 22, and the so-called single path aberration measurement (method in which the aberrations of the eye has an influence on only the light receiving side) is established. In order to satisfy the above, the lens 13 is disposed such that the conjugated point of the retina of the real light beam coincides with the front focal position, and further, in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, in the single path measurement, the diameters of the light beams are different from each other, and the beam diameter of the light beam 15 is set to be rather small as compared with the light beam 24. Specifically, the beam diameter of the light beam 15 is, for example, about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis are applied to the Hartmann plate 22. Besides, in general, with respect to the measuring object part (the eye 60 to be measured), in order to measure a spherical component of the eye 60 to be measured, a third-order astigmatism, and other higher order aberrations, it is necessary to perform the measurement with at least 17 beams through the eye 60 to be measured.

The micro-Fresnel lens is an optical element, and includes, for example, a ring with a height pitch for each wavelength, and a blade optimized for emission parallel to a condensing point. The micro-Fresnel lens here is subjected to, for example, 8-level optical path length variation employing a semiconductor fine working technique, and achieves a high condensing efficiency (for example, 98%).

Besides, the reflected light from the retina 61 of the eye 60 to be measured passes through the afocal lens 42 and the collimate lens 21, and is condensed on the first light receiving part 23 through the Hartmann plate 22. Accordingly, the Hartmann plate 22 includes a wavefront conversion member for converting the reflected light flux into at least 17 beams.

1-2. Electrical System

Figure 3:
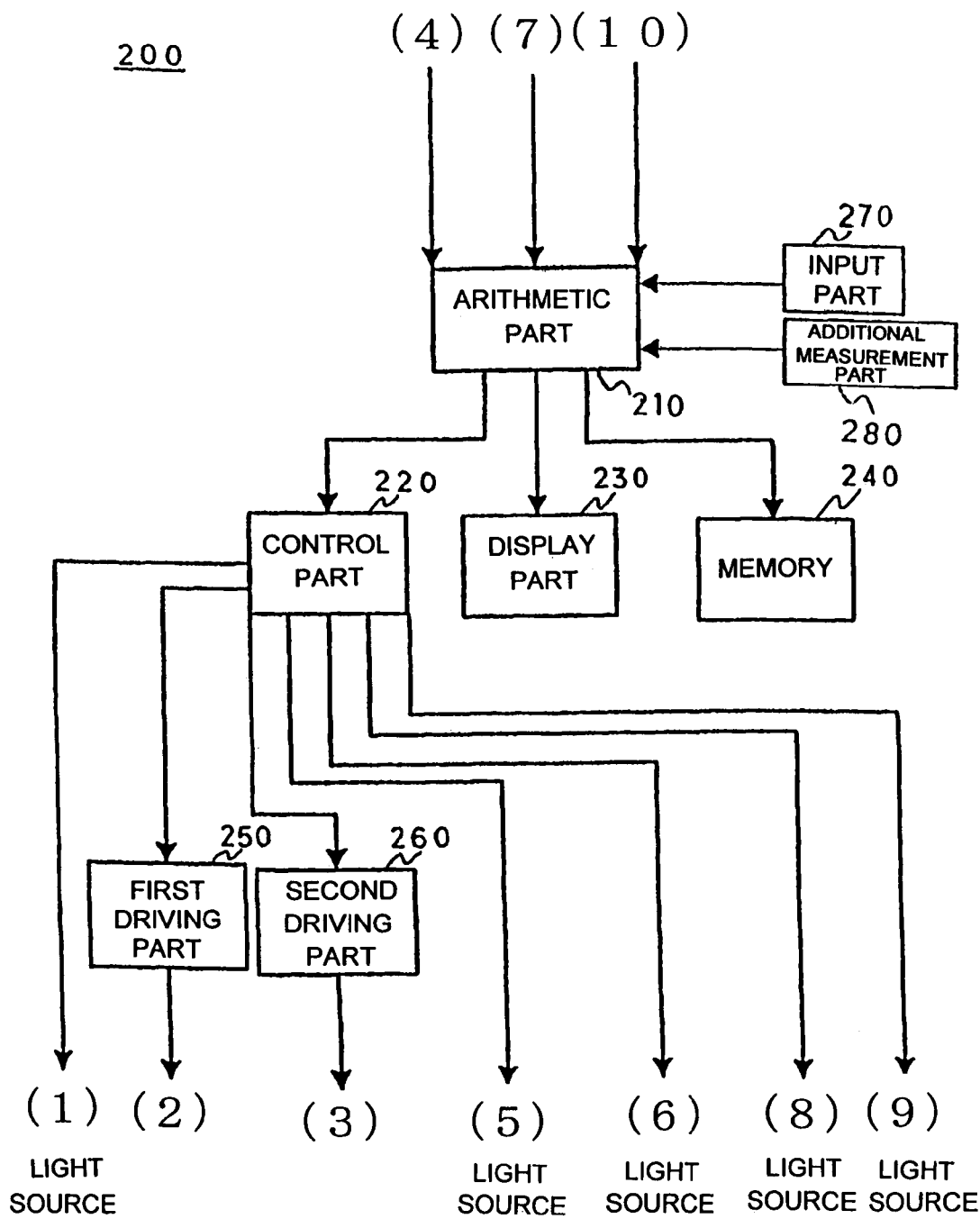
FIG. 3 is a block diagram roughly showing an electrical system 200 of the eye optical characteristic measuring apparatus of the invention.

FIG. 3 is a block diagram roughly showing an electrical system 200 of the eye optical characteristic measuring apparatus of the invention.

The electrical system 200 of the eye optical characteristic measuring apparatus includes, for example, an arithmetic part 210, a control part 220, a display part 230, a memory 240, a first driving part 250, a second driving part 260, an input part 270 and an additional measurement part 280.

The arithmetic part 210 captures the first and the second signals from the first light receiving part 23 and the second light receiving part 35 at the same or substantially same timing, obtains the optical characteristic of the subject eye on the basis of the first signal from the first light receiving part 23, and obtains the corneal shape of the subject eye on the basis of the second signal from the second light receiving part 35. The arithmetic part 210 receives a received light signal (first signal) [4] obtained from the first light receiving part 23, a received light signal (second signal) [7] obtained from the second light receiving part 35, and a received light signal [10] obtained from the third light receiving part 54, and performs an arithmetical operation on the origin of coordinates, a coordinate axis, movement of coordinates, rotation, ocular aberrations, corneal higher order aberrations, Zernike coefficients, aberration coefficients, a Strehl ratio, a white light MTF, a Landolt's ring pattern and the like. Besides, signals corresponding to such calculation results are outputted to the control part 220 for performing the whole control of an electric driving system, the display part 230, and the memory 240, respectively. Further, the arithmetic part 210 obtains a measurable period from the first signal, the second signal, or both the first signal and the second signal and on the basis of a decision factor for measuring timing. The arithmetic part 210 can select a continuous measurement mode, and in the continuous measurement mode, in the case where a measurement fitting condition of the first signal or the second signal is fulfilled, the measurement of the first signal and the second signal can be performed at specified intervals. Besides, in the continuous measurement mode, in the case where the measurement fitting condition of the first signal or the second signal is again fulfilled, the arithmetic part 210 can automatically perform the measurement. Further, the arithmetic part 210 can select (switch) a learning mode (for example, learning mode with respect to a measuring timing). In the case where the learning mode is selected, a measurement fitting condition at the measurement may be stored and is reflected in the setting of the measurement fitting condition of the first signal or the second signal. In this learning mode, for example, the learning mode is turned on at the measurement of a skilled person, the measuring timing at that time is stored, and the elapse of a specified time from a blink may be made a reference to the setting of the measurable period. Besides, the arithmetic part 210 stores a signal of the second light receiving part at the measurement, and can display the signal of the second light receiving part, together with measurement data, on the display part 230. The arithmetic part 210 correlates, for example, the anterior eye image at the measurement with the measurement result to store them in the memory 240, and can display the anterior eye image and the measurement result on the display part 230. Incidentally, the details of the arithmetic part 210 will be described later.

The control part 220 controls lighting and lights-out of the first light source part 11 on the basis of the control signal from the arithmetic part 210, or controls the first driving part 250 and the second driving part 260. For example, on the basis of the signals corresponding to the operation results in the arithmetic part 210, the control part outputs a signal [1] to the first light source part 11, outputs a signal [5] to the Placido's disk 71, outputs a signal [6] to the second light source part 31, outputs a signal [8] to the third light source part 51, outputs a signal [9] to the fourth light source part 55, and outputs signals to the first driving part 250 and the second driving part 260.

The first driving part 250 is for moving the whole first illuminating optical system 10 in the optical axis direction on the basis of, for example, the received light signal [4] inputted to the arithmetic part 210 from the first light receiving part 23, and outputs a signal [2] to a not-shown suitable lens movement means and drives the lens movement means. By this, the first driving part 250 can perform the movement and adjustment of the first illuminating optical system 10.

The second driving part 260 is for moving the whole first light receiving optical system 20 in the optical axis direction on the basis of, for example, the received light signal [4] inputted to the arithmetic part 210 from the first light receiving part 23, and outputs a signal [3] to a not-shown suitable lens movement means, and drives the lens movement means. By this, the second driving part 260 can perform the movement and adjustment of the first light receiving optical system 20.

The input part 270 is for performing various selections of, for example, a measurement mode, a decision factor for measuring timing, a measurable period (range), the number of times of continuous measurements in the case of the continuous mode, and the like. The measurement mode is for selecting an automatic or manual, a single measurement or continuous measurement, or the like. In the case where the manual is selected as the measurement mode, the input part 270 becomes, for example, a finder switch for the manual measurement. The decision factor for measuring timing is such that the acceptance or rejection of measurement is set by a suitable factor using the received light signal (first signal) [4] obtained from the first light receiving part 23, the received light signal (second signal) [7] obtained from the second light receiving part 35, or both the first signal and the second signal.

The additional measurement part 280 performs, for example, a pulse measurement. By the additional measurement part 280, a measurement can be performed in consideration of a pulse. The arithmetic part 210 receives a signal corresponding to a pulse of a person to be measured from the additional measurement part 280, and in accordance with the signal corresponding to the pulse, a subsequent measuring timing can be decided in the substantially same state as the pulse state at the timing point of the initial measurement. Besides, the arithmetic part 210 further receives the signal corresponding to the pulse of the person to be measured from the additional measurement part 280, and in accordance with the signal corresponding to the pulse, a measuring timing can be decided when a specified pulse state is obtained. As stated above, in the arithmetic part 210, the measuring timing can be decided by, for example, the pulse.

Figure 4:
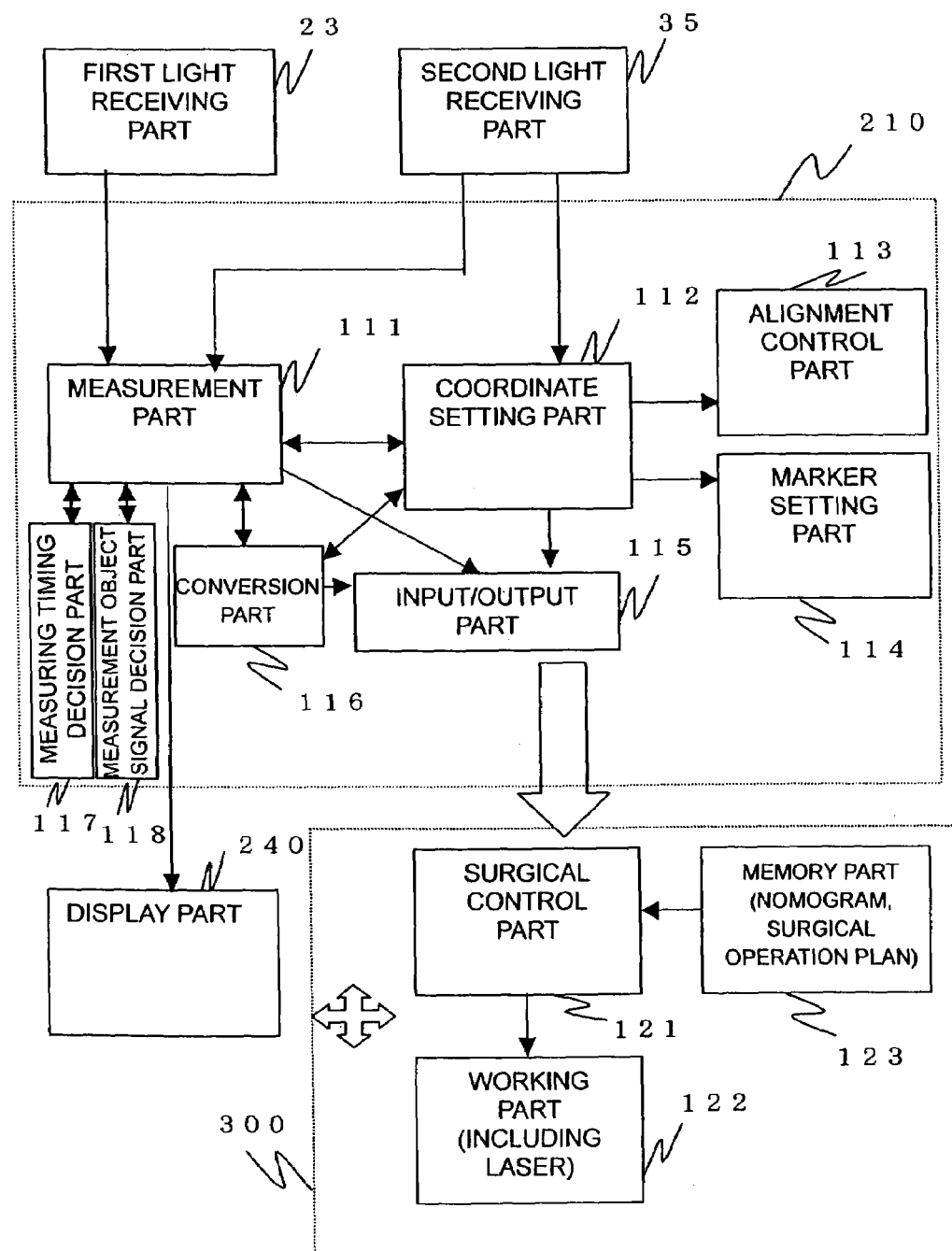
FIG. 4 is a detailed structural view of an arithmetic part of the eye characteristic measuring apparatus of the invention.

FIG. 4 is a detailed structural view of the arithmetic part of the eye characteristic measuring apparatus of the invention. The arithmetic part 210 includes a measurement part 111, a coordinate setting part 112, an alignment control part 113, a marker setting part 114, an input/output part 115, a conversion part 116, a measuring timing decision part 117, a measurement object signal decision part 118, and a visual line detection part 119. Incidentally, either one of the measuring timing decision part 117 and the measurement object signal decision part 118 may be provided. Besides, the visual line detection part 119 may be omitted.

The first light receiving part 23 forms the first received light signal from the received light flux reflected and returned from the retina of the subject eye and guides it to the measurement part 111. The second light receiving part 35 forms the second received light signal including the information of an anterior eye part from the received light flux including a feature portion of the anterior eye part of the subject eye and/or information relating to a marker formed in the anterior eye part of the subject eye, and guides it to the measurement part 111 and the coordinate setting part 112.

The measurement part 111 obtains optical characteristics including the refractive power of the subject eye or the corneal shape on the basis of the first received light signal from the first light receiving part. The measurement part 111 performs the measurement of the eye optical characteristic especially on the basis of the first received light signal from the first light receiving part 23. Besides, the measurement part 111 performs the measurement of the corneal shape, such as corneal topography measurement, on the basis of the second received light signal from the second light receiving part 35. Besides, the measurement part 111 performs an arithmetical operation on the aberrations result, and an arithmetical operation on an ablation amount as the need arises, and outputs the operation results to a surgical apparatus through the input/output part 115. Besides, the measurement part 111 obtains the optical characteristic of the subject eye on the basis of the first signals captured plural times, and obtains the corneal shape of the subject eye on the basis of the second signals captured plural times at the same or substantially same timing from the second light receiving part.

The measurement part 111 captures the first and the second signals from the first light receiving part 23 and the second light receiving part 35 at the same or substantially same timing, obtains the optical characteristic of the subject eye on the basis of the first signal from the first light receiving part 23, and obtains the corneal shape of the subject eye on the basis of the second signal from the second light receiving part 35.

The coordinate setting part 112 converts signals of a first and a second coordinate systems corresponding to the pupil of the subject eye included in the first and the second received light signals into signals of reference coordinate systems, respectively. The coordinate setting part 112 obtains a pupil edge and a pupil center on the basis of the respective signals of the first and the second coordinate systems.

Besides, the coordinate setting part 112 decides the origin of coordinates and the direction of a coordinate axis on the basis of the second received light signal including feature signals of the anterior eye part of the subject eye. Besides, the coordinate setting part 112 obtains the origin of the coordinates, and the rotation and movement of the coordinate axis on the basis of at least one of the feature signals of the anterior eye part of the subject eye of the second received light signal, and correlates the measurement data with the coordinate axis. Incidentally, the feature portion includes at least one of a pupil position, a pupil center, a corneal center, an iris position, an iris pattern, a pupil shape, and a limbus shape. For example, the coordinate setting part 112 sets the origin of the coordinates, such as the pupil center or the corneal center. The coordinate setting part 112 forms the coordinate system on the basis of the feature signal corresponding to the image of the feature portion of the anterior eye part of the subject eye included in the second received light signal. Besides, the coordinate setting part 112 forms the coordinate system on the basis of a marker signal included in the second received light signal and concerning a marker provided on the subject eye, and a signal concerning the anterior eye part of the subject eye. The coordinate setting part 112 can decide the origin of the coordinates and the direction of the coordinate axis on the basis of the second received light signal including the marker signal. The coordinate setting part 112 obtains the origin of the coordinates on the basis of the marker signal in the second received light signal, obtains the rotation and movement of the coordinate axis on the basis of any one of the feature signals of the anterior eye part of the subject eye in the second received light signal, and can correlate the measurement data with the coordinate axis. Alternatively, the coordinate setting part 112 obtains the origin of the coordinates on the basis of at least one of the feature signals concerning the anterior eye part in the second received light signal, obtains the rotation and movement of the coordinate axis on the basis of the marker signal in the second received light signal, and may correlate the measurement data with the coordinate axis. Alternatively, the coordinate setting part 112 obtains the origin of the coordinates and the rotation and movement of the coordinate axis on the basis of at least one of the feature signals of the anterior eye part of the subject eye in the second received light signal, and may correlate the measurement data with the coordinate axis.

The conversion part 116 correlates the first and the second optical characteristics of the subject eye obtained by the measurement part 111 through the respective reference coordinate systems formed by the coordinate setting part and combines them. Besides, the conversion part 116 performs conversion to the reference coordinate system by making the pupil center obtained by the coordinate setting part 112 the origin.

One of, two or more of, or all of the first illuminating optical system 10, the first light receiving optical system 20, the second light receiving optical system 30, the common optical system 40, the adjusting optical system 50, the second illuminating optical system 70, and the second light sending optical system 80 are suitably provided in an alignment part of the optical system 100. The alignment control part 113 can move this alignment part according to the movement of the subject eye and in accordance with the operation result of the coordinate setting part 112 on the basis of the second received light signal obtained by the second light receiving part. On the basis of the coordinate system set by the coordinate setting part 112, the marker setting part 114 forms a marker correlated with the coordinate system on the anterior eye part of the subject eye. The input/output part 115 is an interface for outputting data and operation results of the aberration amount, the origin of coordinates, the coordinate axis, the rotation and movement of the coordinate axis, and the ablation amount to the surgical apparatus. A display part 240 displays the optical characteristic of the subject eye obtained by the measurement part 111 in relation to the coordinate system formed by the coordinate setting part.

A surgical apparatus 300 includes a surgical control part 121, a working part 122, and a memory part 123. The surgical control part 121 controls the working part 122, and controls a surgical operation such as keratectomy. The working part 122 includes a laser for the surgical operation such as keratectomy. The surgical memory part 123 stores data for the surgical operation, such as data concerning cutting, a nomogram, a surgical schedule and the like.

The measuring timing decision part 117 decides, on the basis of the first and/or the second signal, measuring timings of the first signal and the second signal as the object on which the measurement operation is performed. The measuring timing decision part 117 uses, as a specified decision factor for measuring timing, at least one of a blink of the subject eye, a poor tear film, lack of a pupil diameter, and a poor opening eyelid. The measuring timing decision part 117 judges the suitability of a measurement by a first decision factor for measuring timing on the basis of the first signal, and judges the suitability of a measurement by a second decision factor for measuring timing on the basis of the second signal, and decides the measuring timings of the first signal and the second signal in accordance with these judgments. The measuring timing decision part 117 can make the first decision factor for measuring timing at least one of the blink of the subject eye, the poor tear film, the lack of the pupil diameter, and the opening eyelid, and can make the second decision factor for measuring timing at least one of the blink of the subject eye, the poor tear film, the lack of the pupil diameter, the poor opening eyelid, and fixation disparity, the measuring timing decision part 117 detects the blink of the subject eye on the basis of the first signal and/or the second signal, decides a specified measurable range on the basis of the timing of the blink, and further decides the measuring timings of the first signal and the second signal on the basis of the suitability of the measurement according to the decision factor for measuring timing of the first signal or the second signal. At this time, as the decision factor for measuring timing concerning the first signal or the second signal, at least one of a pupil diameter, a state of a tear film, and an opening degree of an eyelid can be selectively set. Further, the measuring timing decision part 117 decides the measuring timings of the first signal and the second signal at the same or substantially same timing. When the measurement fitting conditions of the first signal and the second signal are fulfilled, the measuring timing decision part 117 causes the measurement part 111 to automatically start a measurement or permits the measurement.

The measurement object signal decision part 118 decides the first signal and the second signal as the object on which the measurement operation is performed. The measurement object signal decision part 118 judges the suitability of the measurement according to the specified decision factor for measuring timing on the basis of the first signal and/or the second signal, and decides the measurement object signal of the first signal and the second signal in accordance with this. The specified decision factor for the measurement signal can be made at least one of a blink of the subject eye, a lack of a pupil diameter, and a poor opening eyelid. The measurement object signal decision part 118 judges the suitability of the measurement according to the first decision factor for measuring timing on the basis of the first signal, judges the suitability of the measurement according to the second decision factor for measuring timing on the basis of the second signal, and decides the measuring timings of the first signal and the second signal in accordance with these judgments. At this time, the first decision factor for measuring timing can be made at least one of the blink of the subject eye, the poor tear film, the lack of the pupil diameter, and the poor opening eyelid, and the second decision factor for measuring timing can be made at least one of the blink of the subject eye, the poor tear film, the lack of the pupil diameter, the poor opening eyelid, and the fixation disparity.

The visual line detection part 119 detects a visual line direction of the subject eye on the basis of the third illuminating optical system for illuminating the cornea of the subject eye with a parallel light flux, and the position of the illuminating light by the third illuminating optical system from the second light receiving part 35. By further providing the visual line detection part 119, the measurement part 111 of the arithmetic part 210 may suppress the measurement when the fixation disparity is detected by the visual line detection part.

2. Eye Optical Characteristic Measurement and Correlation of Plural Coordinate Systems Next, a flowchart concerning determination of coordinates by the eye characteristic measuring apparatus of the invention will be described.

Figure 5:
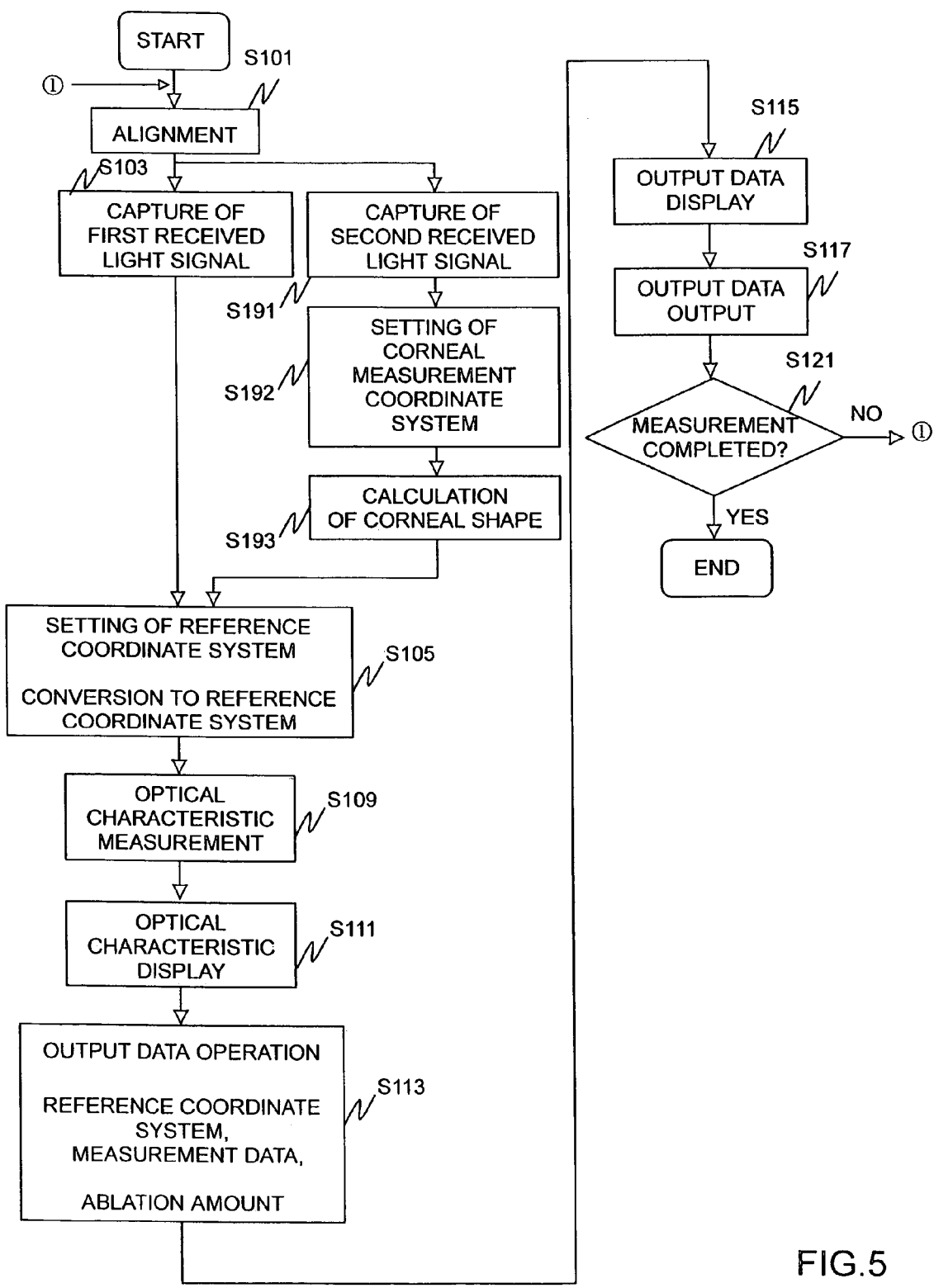
FIG. 5 is a flowchart showing an operation of the eye optical characteristic measuring apparatus of the invention.

FIG. 5 is a flowchart showing the operation of the eye characteristic measuring apparatus of the invention. FIGS. 6 and 7 are explanatory views (1) and (2) concerning the eye characteristic measurement.

First, the signal from the second light receiving part 35 is formed as an anterior eye image on a monitor screen of the display part 230. At step S101, an alignment in the horizontal direction (optical axis of the corneal vertex and the apparatus, XY direction) is performed while the reflected light of the vertex of the cornea is made an alignment target, and an alignment in the vertical direction (depth direction, Z direction) is performed by a Z-alignment apparatus.

Figure 8:
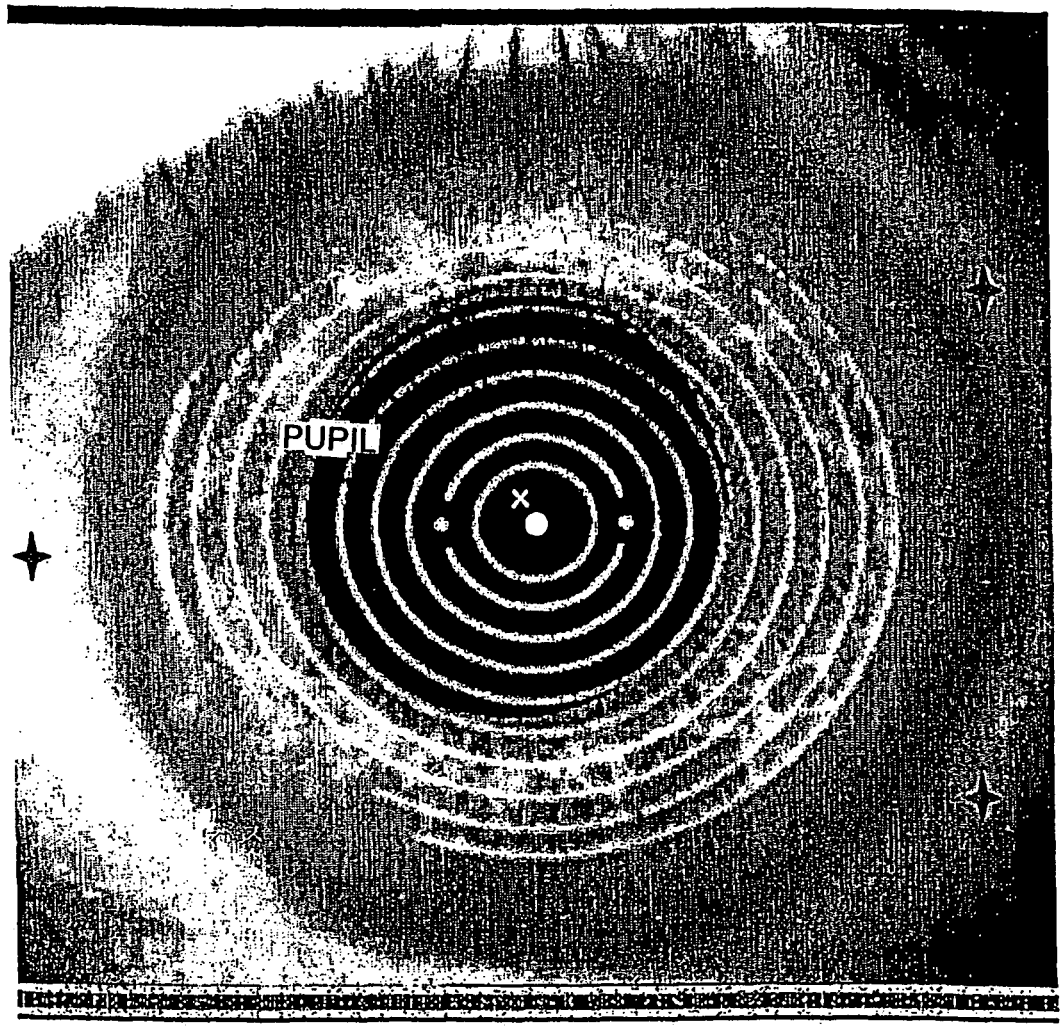
FIG. 8 is an explanatory view of an anterior eye image.

FIG. 8 is an explanatory view of the anterior eye image. In the drawing, "×" denotes the pupil center, "○" denotes the corneal vertex (center), and an asterisk mark denotes an alignment marker. An actual alignment marker may have a different shape such as a circle. The pupil center is mainly treated as the origin of the surgical apparatus. The corneal center (vertex) is mainly treated as the center of the CCD or the machine. As shown in the drawing, at the step S101, in addition to the image of the Placido's disk 1, the light from the second light source part 31 appears as a bright point in the vicinity of the corneal vertex of the subject eye. While the anterior eye image of the subject eye is observed, the alignment of the eye characteristic measuring apparatus is performed in the XY direction with respect to the subject eye, and at this time, the alignment in the Z direction is also performed by the adjusting optical system 50.

Next, in the first measurement system, at step S103, the first received light signal concerning the Hartmann image is captured by using the first light receiving part 23 of the low noise CCD or the like, and the barycenter of the respective spots of the Hartmann image is obtained by a method of image processing. The obtained barycenter is made to correspond to a reference point by using a method of image recognition or calculation geometry. The processing to this point is performed by the first light receiving part 23 in the first coordinate system (see the upper drawing of FIG. 6(A)).

On the other hand, in the second measurement system, as indicated at step S191, at the substantially same time as the capture of the first received light signal, the capture of the second received light signal concerning the anterior eye image is also performed by the second light receiving part 35. After the capture of the second received light signal, the positions of ring images photographed substantially concentrically with the bright spot of the corneal vertex reflection are analyzed by using the method of image processing. With respect to the positions of the rings, for example, approximately 256 points are acquired over 360 degrees on the circumference.

Next, at step S192, a corneal measurement coordinate system is set. Since the position of the corneal vertex is sometimes deviated from the optical axis of the measuring apparatus, the position of the obtained ring image is converted into a value on the coordinate system in which the corneal vertex is made the origin, and the number of pixels of the CCDs of the second light receiving part 35 is changed into an actual distance in consideration of the magnification of the optical system. The coordinate system for the corneal measurement is called a second coordinate system (see the upper drawing of FIG. 6(B)). At step S193, a tilt of the cornea is calculated from the positions of the rings obtained at the step S191 and by using the second coordinate system calculated at the step S192.

At step S105, the Hartmann image and the anterior eye image measured in the first and the second coordinate systems in this way are respectively converted into those in reference coordinate systems in which the pupil center is the origin (see the lower drawing of FIGS. 6(A), (B)).

At the step S105, with respect to the first measurement system, the pupil edge on the Hartmann wavefront sensor image obtained from the first light receiving part 23 can be obtained by the image processing. Here, since the obtained pupil edge is influenced by aberrations and is distorted, the arithmetic part 210 corrects the shape of the pupil edge from the relation between the Hartmann dot image and the reference point obtained at the step S103. For example, the arithmetic part 210 obtains a function for correction by the least squares approximation similarly to the case where the wavefront aberrations are obtained from the Hartmann wavefront sensor, inputs the position of the pupil edge on the Hartmann wavefront sensor image to the function obtained now, and calculates the position of the correct pupil edge. Besides, when the correct position of the pupil edge is obtained, the arithmetic part 210 causes a pixel in the inside of the pupil to have 1, and causes the outside to have 0 to obtain the barycenter, so that the position of the pupil center in the CCD coordinate system is obtained. For example, the center of a circle or an ellipse can be made the barycenter. In this way, as shown in the upper drawing of FIG. 6(A), the pupil center (×) is measured. The conversion from the first coordinate system to the newly defined reference coordinate system is performed by moving the origin of the reference coordinate to the pupil center, and by changing the number of pixels of the CCDs into the actual distance by the magnification of the optical system.

Besides, at the step S105, with respect to the second measurement system, the arithmetic part 210 obtains the pupil edge by the image processing from the coordinate system for the corneal measurement obtained from the second light receiving part 35 and set by the processing of the step S192, that is, the second coordinate system as well, and calculates the position of the pupil center in the second coordinate system. In this way, the pupil center (×) is obtained, and the upper drawing of FIG. 6(B) is measured. At this time, the conversion from the second coordinate system to the reference coordinate system is the movement of the pupil center. At the measurement of an abnormal eye such as keratoconus, in the case where a part of the pupil edge is chipped in the Hartmann wavefront sensor image, measures can be taken by performing estimation of the chipped portion or the like to obtain the barycenter.

The reference coordinate system converted from the first coordinate system and the reference coordinate system converted from the second coordinate system in this way become the same reference coordinate system in principle (see the respective lower drawings of FIGS. 6(A) and 6(B)).

Next, the optical characteristic is obtained on the basis of the first or the second received light signal (S109). Here, the optical characteristic is, for example, aberrations (cornea, intraocular, ocular) refractive power, corneal shape and the like. That is, at the step S109, with respect to the first measurement system, the arithmetic part 210 calculates the optical characteristic by the measurement principle of the Hartmann wavefront sensor. The wavefront aberrations of the ocular optical system (ocular higher order aberrations) are obtained by this (see FIG. 7(A)). Besides, with respect to the second measurement system, since the tilt of the cornea is obtained, the height of the cornea is calculated from this by the arithmetic part 210, and the optical characteristic is calculated by treating the cornea similarly to an optical lens. The wavefront aberrations occurring in the cornea (corneal higher order aberrations) are obtained here (see FIG. 7(B)).

Figure 7A:
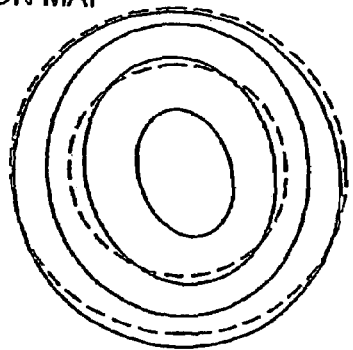
FIGS. 7(A)–7(C) are explanatory views (2) of eye characteristic measurement.
Figure 7B:
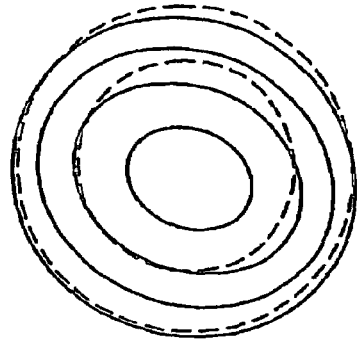
Figure 7C:
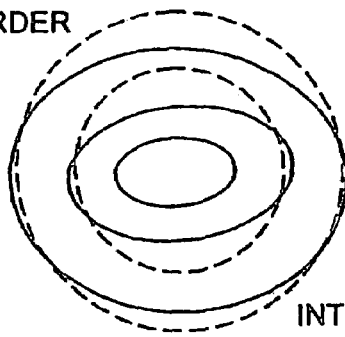

Next, the measured optical characteristic is displayed (S111). At the step S111, with respect to the display of the optical characteristic by the display part 240, as shown in FIG. 7, the ocular higher order aberration map concerning the first measurement system and the corneal higher order aberration map concerning the second measurement system are separately displayed, and at the same time, (differential higher order aberration map)=(ocular higher order aberration map)−(corneal higher order aberration map)

is also displayed (see FIG. 7(C)). This differential higher order aberration map optically indicates an influence on the aberrations of the internal optical system except for the front of the cornea of the ocular optical system, and is a map very useful for diagnosis of a disease in which abnormality occurs in the refractive index distribution of a crystalline lens, for example, a cataract.

Next, output data is calculated (S113). As the output data, for example, data of the reference coordinate system, measurement data, an aberration amount itself of the subject eye, optical characteristic data, an ablation amount required for cutting by a surgical apparatus, and the like are obtained by performing an arithmetical operation. Next, these output data are displayed (S115). Further, as the need arises, these output data are outputted (S117). Here, the form of the output includes, for example, following modes.

[1] The form which is an off-line mode and in which the output is made through a recording medium such as a floppy disk or a CD-ROM, or through an interface of a signal line, wireless line or the like, and then, a surgical operation is performed at a different timing.

[2] The form in which the output data is connected to the surgical apparatus 300 on-line through an interface of a signal line or the like, and at a surgical operation, the optical characteristic of the subject eye is measured continuously or by switching.

As described above, after the data output, if the measurement is not completed, it is repeated, and if completed, the measurement is ended (S121).

Here, a method of obtaining the pupil edge from the Hartmann image will be described. As a first method of obtaining the pupil edge from the Hartmann image, the pupil edge can be obtained by obtaining a polygon circumscribing the Hartmann spot or an ellipse close to that. A second method uses a fact that because of an influence of a diffused component from an eye, or since the Hartmann plate is a diffraction optical element and 0-th order light is transmitted, a portion of the Hartmann image corresponding to the pupil is brighter than the other background. Thus, by detecting the edge of the bright portion, the edge portion of the pupil can be detected.

FIG. 9 is an explanatory view for obtaining the pupil edge from the Hartmann image. FIG. 9(A) shows an example of the measured Hartmann image. As shown in FIG. 9(B), this is compared with the brightness of the Hartmann spot measured at a previously decided threshold along a line. Next, as shown in FIG. 9(C), when this processing is performed over the whole Hartmann image, the pupil edge can be detected.

Incidentally, the origin of coordinates and the axial direction are decided by using the feature signals included in the second received light signal indicating the image of the anterior eye part of the subject eye including the feature portion, and the reference coordinate system can be set. Here, as the feature portion of the anterior eye part of the subject eye, for example, a pupil position, an iris position, an iris pattern, a pupil shape, a limbus shape, a marker (in the case where there is a marker) formed on the anterior eye part of the subject eye and the like can be enumerated. In the reference coordinate system, it is preferable to adopt the origin of coordinates used in the surgical apparatus 300, and it is obtained from, for example, the pupil position of the subject eye, the iris position of the subject eye, the pupil shape, the limbus shape, the pattern of the iris of the subject eye (iris marking) or the like. As the origin of coordinates, the pupil center, the corneal center or the like is conceivable. In the case where the marker is formed, the coordinate axis can be set by, for example, a straight line passing through the marker and the pupil center. In the case where the marker is formed, the rotation and movement of the coordinate can be measured by, for example, the rotation and movement of the marker.

Figure 10A:
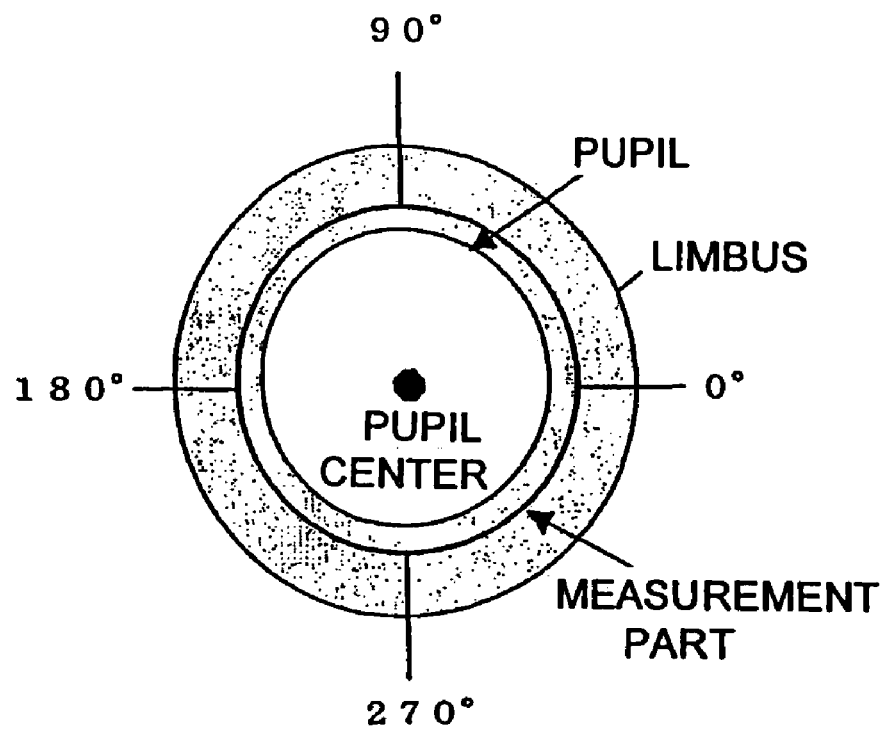
FIGS. 10(A) and 10(B) are explanatory views of measurement of coordinate axis and rotation.
Figure 10B:
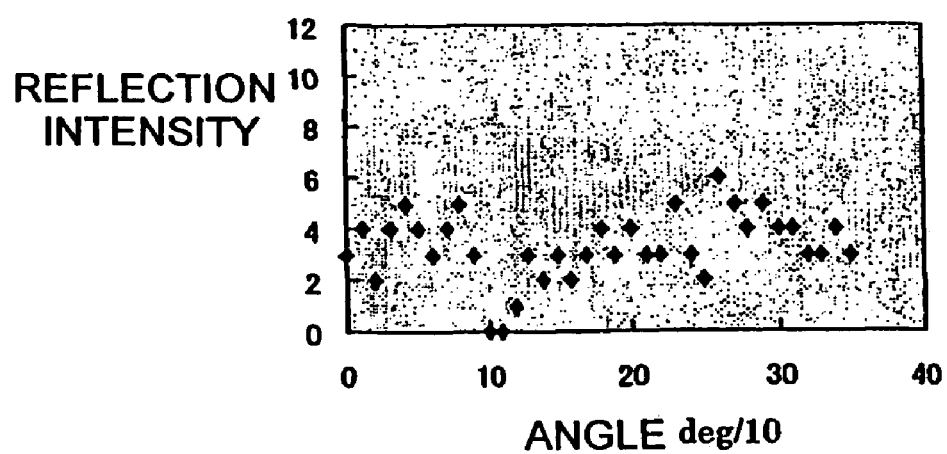

Besides, the coordinate axis and the rotation (cyclotorsion) can be measured by the pattern of the pupil iris (iris marking) in addition to the marker. Here, FIG. 10 is an explanatory view concerning the measurement of the coordinate axis and rotation. First, as shown in FIG. 10(a), for example, a pattern is analyzed using reflection intensity or the like on the ring around the pupil center as the center. Then, as shown in FIG. 10(b), the pattern of the reflection intensity with respect to an angle are prepared. By this pattern, the coordinate axis can be set. Besides, the analyzed pattern is matched on the circumference, and the coordinate rotation can be measured. That is, when the eye is rotated (cyclo-torsion), a graph of such intensity is horizontally shifted by the rotation angle. The amount of the horizontal shift can be obtained by the largest angle of correlation between the respective measurement values and the reference graph.

Figure 11:
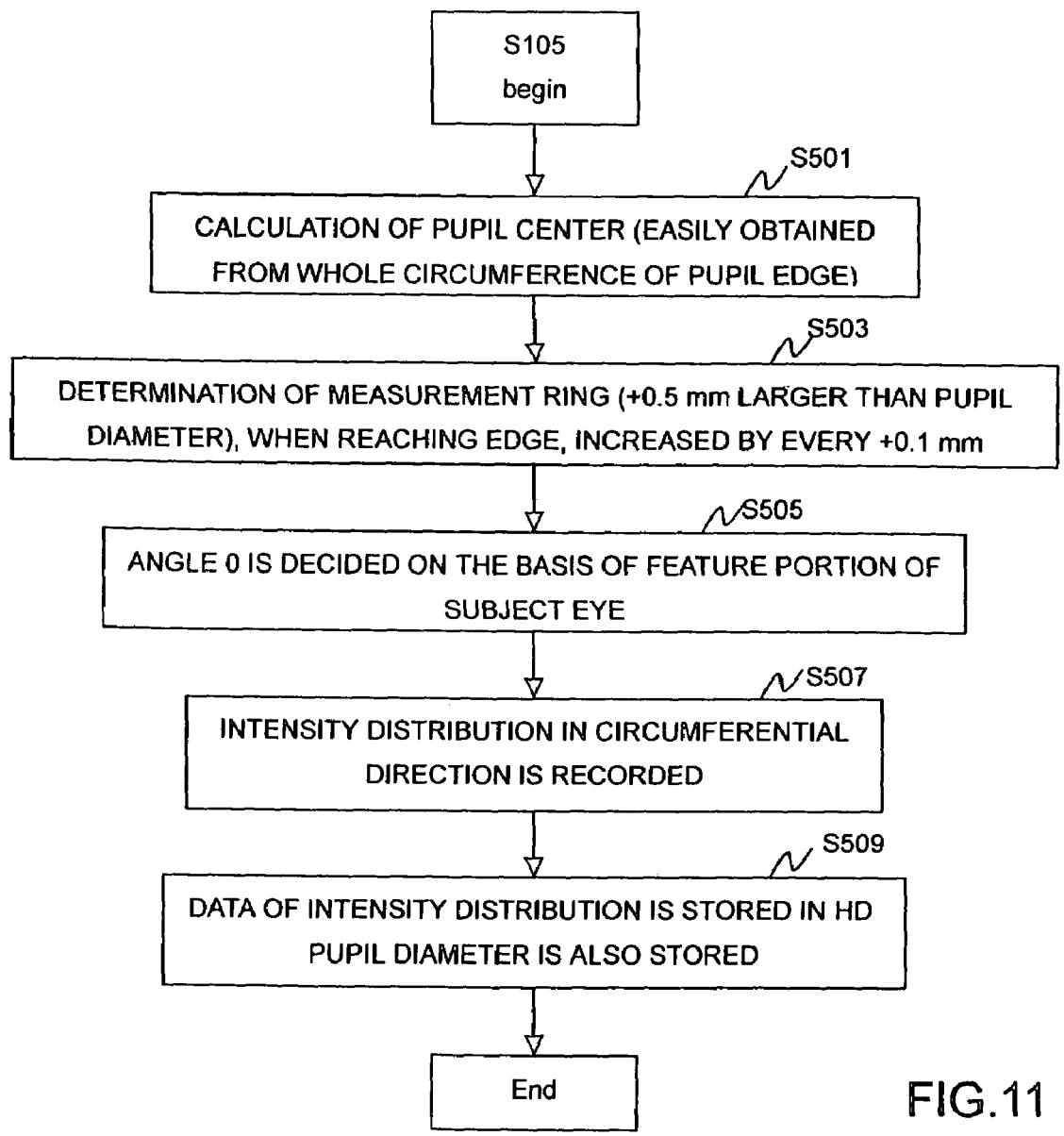
FIG. 11 is a flowchart for performing pupil center calculation or measurement of measurement rings.

FIG. 11 is a flowchart for performing pupil center calculation or measurement of measurement rings.

First, in order to decide the origin of coordinates, the pupil center is calculated (easily obtained from the whole circumference of the pupil edge) (S501). Next, the measurement ring is decided (for example, +0.5 mm larger than the pupil diameter). When reaching the edge, it is increased by, for example, every +0.1 mm (S503). Next, in order to decide the coordinate axis, the angle is decided on the basis of the feature portion of the subject eye (S505). Next, the intensity distribution in the circumferential direction is recorded (S507). Next, the data of the intensity distribution is stored in a hard disk (HD) or the like, and the pupil diameter is also stored (S509).

Figure 12:
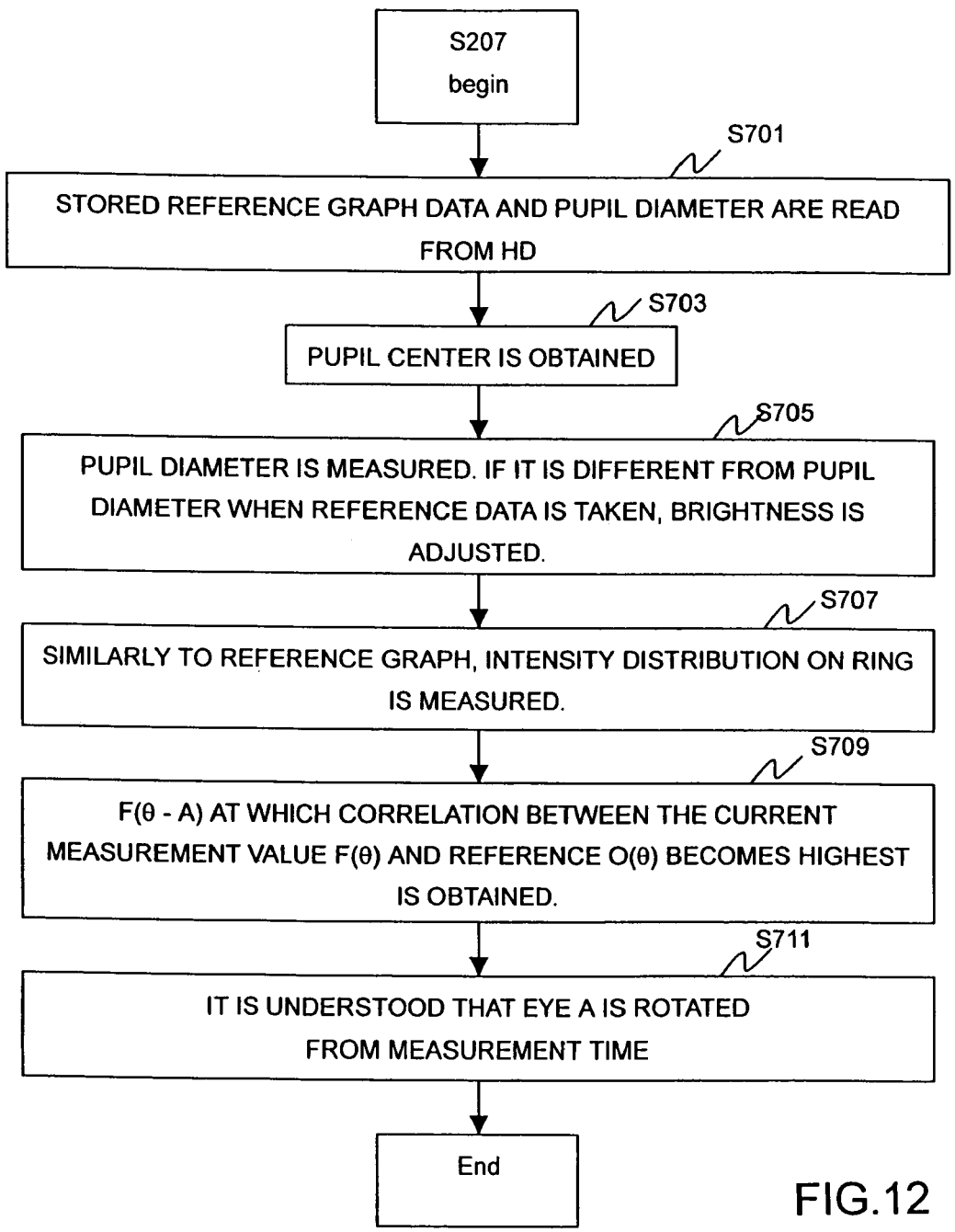
FIG. 12 is a flowchart for confirming a difference between a measurement coordinate system and a reference coordinate system.

Here, FIG. 12 is a flowchart for confirming a difference between the measurement coordinate system and the reference coordinate system. This is the detailed flowchart of step S207, in which the pupil center calculation, the measurement of the measurement ring and the like are subjected to correlation processing, and a conformable coordinate position is obtained.

First, stored reference graph data $O(\theta)$ and a pupil diameter are read from the memory 240 of the hard disk (HD) or the like (S701). As the reference graph data $O(\theta)$, for example, the intensity distribution on the ring shown in FIG. 10 can be used. Next, the pupil center is obtained on the basis of the read digital (S703). Next, the pupil diameter is measured, and when it is different from the pupil diameter at the time when the reference graph data $O(\theta)$ is obtained, the brightness is adjusted (S705). Next, similarly to the reference graph data, the measured graph data $F(\theta)$, for example, the intensity distribution on the ring is measured (S707). Next, measured graph data $F(\theta-A)$ rotated by an angle A is obtained in which the correlation between the graph data $F(\theta)$ measured this time and the reference graph data $O(\theta)$ becomes highest (S709). In this way, it is understood that the eye is rotated by the angle A from the time of measurement (S711).

Next, a modified example of the invention will be described.

In the foregoing embodiment, in the second measurement system, although the description has been given of the case where the anterior eye part is observed and the corneal shape is measured, only positioning is performed through the observation of the anterior eye part by the second measurement system, and the structure relating to the measurement of the corneal shape can be omitted. In this case, by using the second measurement system, the eye to be measured is positioned to a specified position. Next, the second received light signal is obtained from the second light receiving part of the second measurement system through the first received light signal from the first light receiving part of the first measurement system. In the arithmetic part, on the basis of the first received light signal and/or the second received light signal, correlating of the coordinate axis (coordinate origin position, rotation and/or movement of coordinate axis) is performed, and the first optical characteristic obtained from the first measurement system can be outputted as a desired coordinate system. As a specific example, the optical axis of the first measurement system and that of the second measurement system are made to coincide with each other, and in the second measurement system, the eye to be measured is positioned to a specified position by using the bright point of the corneal vertex appearing in the anterior eye image. Next, the second received light signal is obtained from the second light receiving part of the second measurement system through the first received light signal from the first light receiving part of the first measurement system. Then, in the arithmetic part, correlating of the coordinate axis (coordinate position origin, rotation and/or movement of the coordinate axis) is performed on the basis of the first received light signal and/or the second received light signal, and the first optical characteristic obtained from the first measurement system can be outputted as the coordinate system of the pupil center.

In this example, the positioning of the subject eye is performed by using the second measurement system and using the bright point of the corneal vertex, and the arithmetic part converts the first optical characteristic obtained from the first measurement system into the coordinate system of the pupil center through the respective received light signals. By this, the data of the first optical characteristic can be used as the coordinate system of the pupil center.

3. Eye Optical Characteristic Measurement and Measuring Timing

Here, a decision factor for measuring timing (factor) which can be detected by the foregoing first signal and second signal will be described. Incidentally, here, among various arithmetical operations performed by the arithmetic part 210, a measurement operation concerning the first signal and the second signal will be mainly described.

FIG. 13 is an explanatory view of the decision factor for measuring timing relating to the first signal and the second signal.

A table 271 is a table showing the decision factor for measuring timing which can be detected by the first signal and the second, and the decision factor for measuring timing includes, for example, a blink, a tear film, a pupil diameter, an eyelid opening, and a fixation state. Besides, with respect to the fixation state, according to whether the pupil center is within a specified distance from the vertex or is largely deviated therefrom, it is possible to judge the fitness as to whether measurement can be performed or not. Besides, a ⊚ mark, a ○ mark, a Δ mark, and a × mark in the drawing given to the respective decision factors for measuring timing of the first signal and the second signal respectively denote good measurement, measurability, poor measurement, and non-measurability according to the respective signals.

A table 272 is a table for indicating a fitting condition suitable for measurement of a case where for example, the same decision factor for measuring timing is detected by different signals, that is, the first and the second signal, and the decision factor for measuring timing includes, similarly to the table 271, a blink, a tear film, a pupil diameter, an eyelid opening, and a fixation state. Besides, here, as the fitting condition, the fixation state is not suitable (–), and the others are good (⊚). Besides, a Table 273 is a table for indicating a fitting condition in the case where for example, different decision factors for measuring timing or same decision factors for measuring timing are detected by different signals, and as a decision factor for measuring timing, an inner abnormality which can be detected by only the first signal is added as the decision factor, and the fitting condition is indicated by combination of these decision factors for measuring timing. Besides, in the case where the same decision factor for measuring timing (blink, tear film, pupil diameter, eyelid opening, etc.) is detected by the first and the second signals, the fitting condition becomes good (⊚). Besides, in the case where different decision factors for measuring timing are detected by the first and the second signals, it becomes usable (○) as the fitting condition by the illustrated combination. Incidentally, here, since it is supposed that the fixation state can not be measured with high accuracy by the first signal, that the fixation state by the first signal is used as the decision factor for measuring timing does not fit to the condition (–).

Here, with respect to a suitability judgment of measurement according to the decision factor for measuring timing of the first signal, the description will be made while the arithmetic part 210 and the respective decision factors for measuring timing shown in the tables 271 to 273 are correlated with each other. Incidentally, the input part 230 can suitably select a case where the decision factor for measuring timing of the first signal is not set and a case where it is set. On the basis of the first signal, the arithmetic part 210 counts, for example, the number of region points received by the first light receiving part 23 and exceeding a predetermined level, or the number of signal levels received by the first light receiving part 23 and having peak levels exceeding a predetermined value. By this, the arithmetic part 210 can judge whether sufficient data to obtain measurement results can be finally obtained. The arithmetic part 210 can judge the suitability of the measurement, for example, in a manner as described below (see the tables 271 to 273).

By detecting whether the first signal level is instantaneously lowered on the whole, it is judged that there is a blink.

By detecting whether the first signal level is lowered at a partial periphery, it is judged whether or not the eyelid opening is sufficient.

By detecting whether there is a fluctuation in the first signal level, it is judged whether or not the tear film is unstable.

By detecting whether the first signal level is lowered at a peripheral part, it is judged whether or not the pupil diameter is contracted. Incidentally, in the eye characteristic measuring apparatus of this embodiment, with respect to miosis, since the near-infrared light flux is used as the light source, it is not bright and miosis does not occur, and therefore, a continuous measurement can be performed.

Next, a suitability judgment of measurement according to the decision factor for measuring timing of the second signal will be described while the arithmetic part 210 and the respective decision factors for measuring timings shown in the tables 271 to 273 are correlated with each other. Incidentally, the input part 230 can select, for example, one of or a combination of two or more of the decision factors for measuring timings on the basis of the second signal. The decision factor for measuring timing of the second signal by the arithmetic part 210 includes a blink, a pupil diameter, a state of a tear film, and an eyelid opening degree. The arithmetic part 210 can judge the suitability of measurement, for example, in a manner as described below (see the tables 271 to 273).

With respect to the blink, immediately after the blink is detected, fixation is made and the measurement can be performed. As the kind of the blink, opening after closing for several seconds, tightly closing, normal slight closing continuously performed several times, and the like are conceivable. As a measurement interval, for example, a time immediately after the blink, or a time after specified seconds on the basis of a past suitable measurable empirical value is conceivable. Incidentally, with respect to this suitable measurable empirical value, it is expected that for example, a measurement value by a skilled person and an analysis result are made to correspond to an interval, so that a specified value for each patient is obtained, and a higher accuracy measurement result is obtained. Further, for example, although miosis temporarily occurs immediately after the blink, the pupil diameter is immediately widened and becomes slightly stable, and a time when the tear film also becomes stable after several ms, is suitable for measurement, and the arithmetic part 210 can calculate the image data of the anterior eye part with high accuracy by using this timing.

By detecting whether or not the pupil is larger than a predetermined diameter (for example, 6φ in a dark field), it is judged whether or not the pupil diameter is suitable.

By detecting the distortion of a pattern 275 according to the Placido's disk 71, or whether the co-axial rings are not discontinuous or a fluid distortion does not occur, it is judged whether or not the tear film is suitable.

By detecting whether or not a ratio of the limbus diameter to the eyelid interval is a predetermined value or more, it is judged whether or not the eyelid opening degree is suitable.

FIG. 14 is an explanatory view of an image received by the first and the second light receiving parts.

A Hartmann image 274 received by the first light receiving part is, for example, an image on the basis of the reflected light from the eye 60 to be measured, and includes plural region points (in the drawing, circular, elliptical, etc.) in the case where the reflected light is received on the first light receiving part 23 as the light flux roughly expanding to the outside through the Hartmann plate 22. With respect to the plural region points included in the Hartmann image 274 of this example, for example, in a portion where the tear film of the eye 60 to be measured is broken, thin or thick, there occurs an elliptical state or a state where the region point itself is not seen, and the arrangement of the plural region points is in an irregular state. Besides, a light signal relating to the Hartmann image 274 is converted into an electrical signal, and is inputted (or captured) as the first signal to the arithmetic part 210.

In the Placido's disk image 275 received by the second light receiving part, in the portion where the tear film of the eye 60 to be measured is broken, thin or thick, the ring of the co-axial rings included in the image is observed to be discontinuous. Besides, a light signal relating to the Placido's disk image 275 is converted into an electrical signal, and is inputted (or captured) as the second signal to the arithmetic part 210.

Next, the operation of the eye characteristic measuring apparatus of the invention will be described with reference to a time chart and a flowchart.

In the arithmetic part 210, with respect to the decision of measuring timing, according to the number (one or not less than two) of decision factors for measuring timing, and the combination of the first signal and the second signal (the first and/or the second signal, the first and the second signals, only the first signal), plural operation patterns are carried out (see after-mentioned four flowcharts). Specifically, the arithmetic part 210 captures, for example, the first signal and the second signal plural times and performs the measurement. Besides, the arithmetic part 210 includes, for example, the measuring timing decision part 117 for deciding the measuring timing, the measurement object signal decision part 118, or both the decision parts, and by this, on the basis of the first and/or the second signal, the suitability of a measurement according to a specified factor for deciding measuring timing is judged, and on the basis of this judgment, the measuring timings of the first signal and the second signal are decided or the measurement object signal is selected.

Hereinafter, respective embodiments will be described.

(1) First Embodiment

Figure 15:
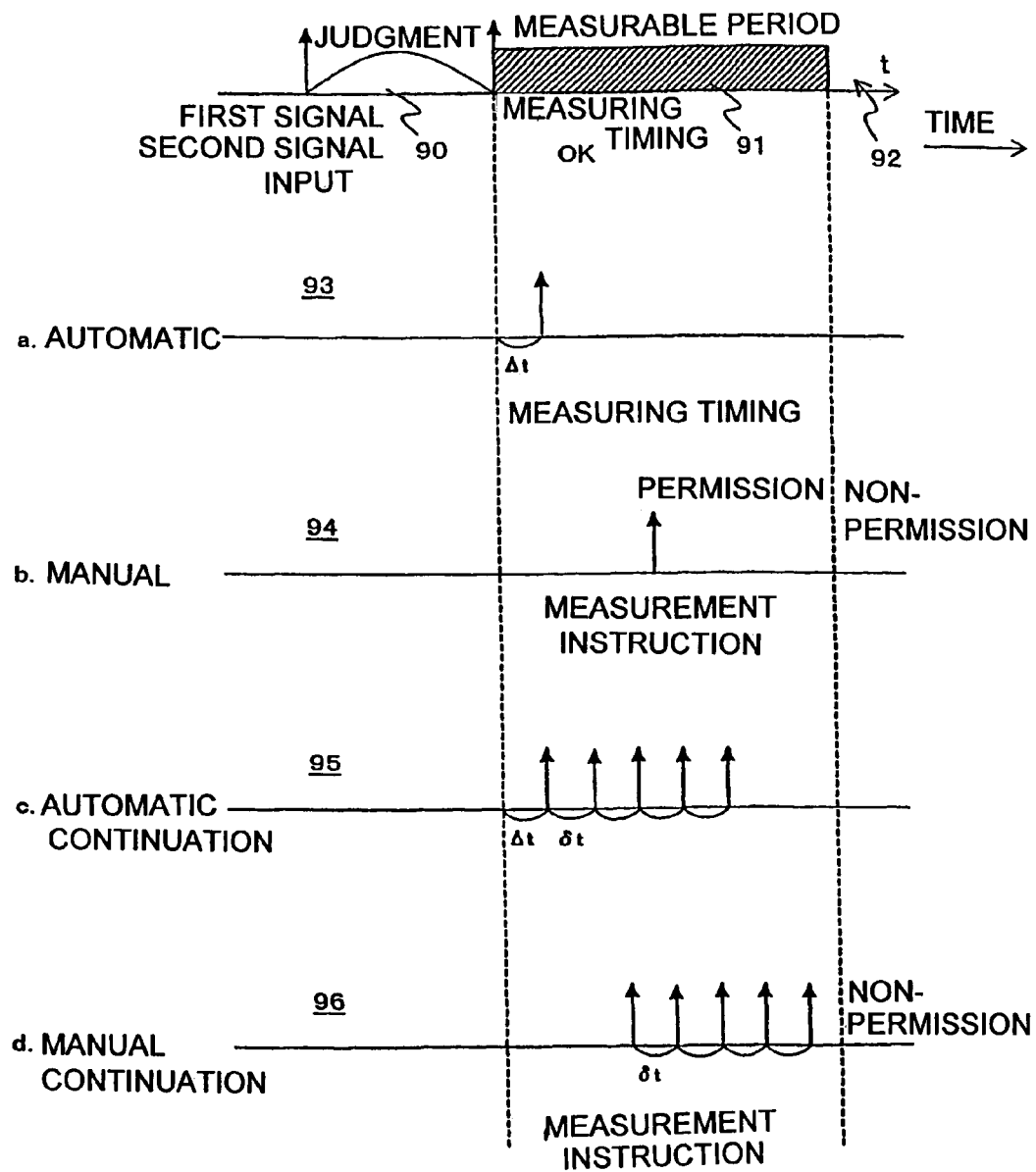
FIG. 15 is an explanatory view of a first embodiment of eye characteristic measurement.

FIG. 15 is an explanatory view of a first embodiment of eye characteristic measurement.

This first embodiment shows an operation of a case where a decision factor for measuring timing is checked by, for example, the first signal and/or the second signal, and a measuring timing is decided.

As a measurement mode, for example, by combination of automatic or manual, and single or continuation, an automatic (single) mode 93, a manual (single) mode 94, an automatic continuous mode 95, and a manual continuous mode can be selected by the input part 270. First, the outline concerning the decision of the measuring timing in the respective measurement modes will be described along the temporal axis. For example, the measuring timing decision part 117 of the arithmetic part 210 receives the first signal, the second signal, or both the signals, and judges whether measurement can be performed (measurement judgment period 90). When it is judged that the measurement can be performed, a specified measurable period 91 is set. The length of the measurable period 91 is previously determined by the input part 270 or the like. After the measurable period 91 has passed, a non-measurable period 92 occurs. Incidentally, as to whether or not the measurement can be perform, the measuring timing decision part 117 makes a judgment by the measurement condition on the basis of the decision factor for measuring timing (factor) of the first signal, the second signal, or both the first signal and the second signal.

The automatic mode 93 is a mode in which the measurement is automatically started at a timing when, for example, all set measurement conditions are satisfied, and when the measurable period 91 occurs, the measurement is performed immediately or after $\Delta t$. Incidentally, the value of $\Delta t$ can be suitably set by the input part 270 or the like. The manual mode 94 is determined as a measurement standby period for a predetermined time from, for example, a time when all set measurement conditions are satisfied, and the measurable period 91 is displayed by display of the suitable display part 230 to the operator. Incidentally, as the display part, for example, a display lamp, a finder switch or the like may be attached to the input part 270. In the measurable period 91, a measurement instruction is issued by the operator using the finder or the like of the input part 270, and the first and the second signals are measured by the arithmetic part 210. Besides, this measurement instruction is permitted in the measurable period 91, but is not permitted in the non-measurable period 92. Incidentally, in the measurable period 91, the measurement can be made plural times by the instruction of the operator.

The automatic continuous mode 95 is a mode in which for example, while a set measurement condition is satisfied, when the measurable period 91 occurs, measurement is performed immediately or after $\Delta t$, and further, the measurement is continuously performed a predetermined number of times (or at a predetermined interval $\delta t$) previously determined by the input part 270 or the like. Incidentally, the value of $\delta t$ can be suitably set by the input part 270 or the like.

In the manual continuous mode 96, for example, a measurable period (here, a measurement standby state) 91 occurs from a time when all set decision factors for measuring timing are satisfied, and the measurement is performed by a measurement instruction by the operator in the measurable period 91, and the measurement is continuously performed a predetermined number of times from the measurement instruction and at a predetermined interval $\delta t$. Incidentally, the value of $\delta t$ can be previously suitably set by the input part 270 or the like. Besides, with respect to the measurement instruction, although the measurement is permitted in the case where the final measuring timing is in the measurable period 91, the measurement is not permitted in the case where it is in the non-measurable period 92.

Figure 16:
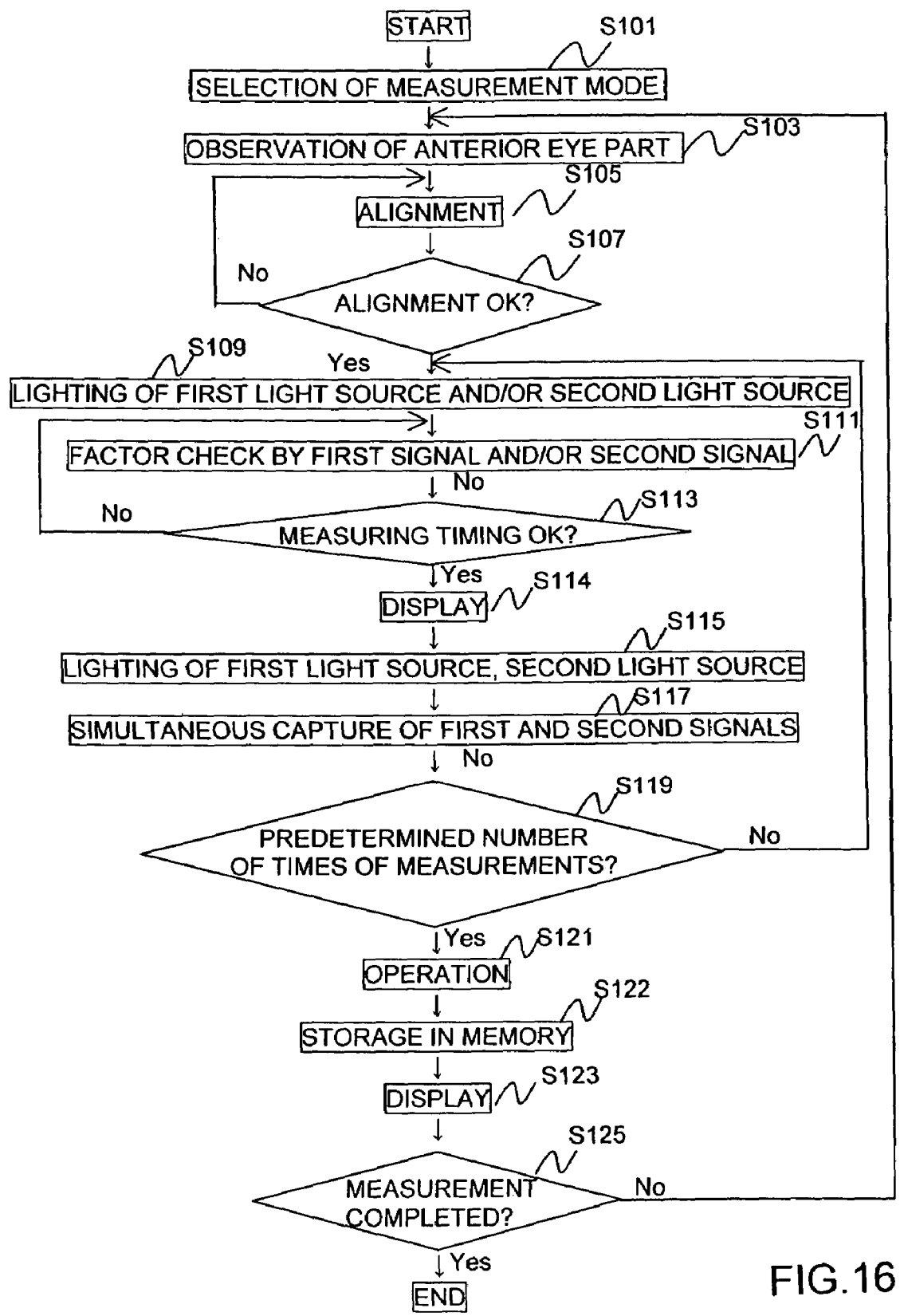
FIG. 16 is a flowchart of the first embodiment showing the operation of the eye optical characteristic measuring apparatus of the invention.

FIG. 16 is a flowchart of the first embodiment showing the operation of the eye optical characteristic measuring apparatus of the invention.

First, the measurement of the eye 60 to be measured as the measuring object is started by the measurer (operator), and the selection of the measurement mode (automatic mode 93, manual mode 94, automatic continuous mode 95, and manual continuous mode 96) is performed by the input part 270 (S101).

The signal from the second light receiving part 35 is formed as the anterior eye image on the monitor screen of the display part 230 (S103). Next, an alignment in the horizontal direction (optical axis of the corneal vertex and the apparatus, XY direction) is performed while the reflected light of the vertex of the cornea is made an alignment target, and an alignment in the vertical direction (depth direction, Z direction) is performed by the Z-alignment apparatus (S105). The optical characteristic measuring apparatus 100 judges whether the alignment is completed (S107). As stated above, if the alignment adjustment is insufficient, a return to the step S105 is made again, and the adjustment of the alignment is performed.

Next, in accordance with the decision factor for measuring timing set by the input part 270, the optical characteristic measuring apparatus 100 switches on the first light source and/or the second light source (S109). In accordance with the decision factor for measuring timing, the measuring timing decision part 117 of the arithmetic part 210 judges whether setting of the measurable period 91 as the period of the measuring timing can be performed (S113). In accordance with the decision conditions corresponding to the respective decision factors for measuring timing, when the measuring timing decision part 117 judges that measurement can be performed, in the measurable period, the arithmetic part 210 makes the measurable period 91 visible or audible by, for example, a lamp or a speaker included in the display part 230 or the input part 270 (S114). Incidentally, at the automatic mode (single, continuous), the step S114 can be omitted.

Next, in accordance with the mode selected in the measurable period, the optical characteristic measuring apparatus 100 switches on the first light source and the second light source (S115). The arithmetic part 210 captures, for example, the first and the second signals simultaneously or substantially simultaneously (S117). In the first measurement system, at the step S103, the first received light signal concerning the Hartmann image is captured by using the first light receiving part 23 of a low noise CCD or the like. On the other hand, in the second measurement system, as indicated at step S191, substantially at the same time as the capture of the first received light signal, the capture of the second received light signal concerning the anterior eye image is also performed by the second light receiving part 35. As described above, in the automatic mode 93, the measurement is performed immediately after the start timing of the measurable period 91 or after Δt, in the manual mode 94, at the measurement instruction time by the finder of the input part 270 or the like in the measurable period 91, in the automatic continuous mode 95, immediately after the start timing of the measurable period 91 or after Δt at a predetermined interval (δt), and in the manual continuous mode 96, after the measurement instruction in the measurable period 91, at a predetermined interval (δt) and plural times.

Next, in order to acquire the first and the second signals sufficient for measurement, the arithmetic part 210 judges whether the measurement is performed a predetermined number of times or more (S119). In the case where the measurement is not performed the predetermined number of times or more at step S119, the arithmetic part 210 is again returned to the step S109. On the other hand, in the arithmetic part 210, in the case where the measurement is performed the predetermined number of times or more at the step S119, the measurement part 111 obtains the optical characteristic on the basis of the first or the second received light signal (S121). Here, the optical characteristic is, for example, aberrations (cornea, internal, ocular) refractive power, corneal shape and the like. That is, at the step S121, with respect to the first measurement system, the arithmetic part 210 calculates the optical characteristic based on the measurement principle of the Hartmann wavefront sensor.

By this, the wavefront aberrations (ocular higher order aberrations) of the ocular optical system are obtained (see FIG. 7(A)). Besides, with respect to the second measurement system, since the tilt of the cornea is obtained, the height of the cornea is calculated from this by the arithmetic part 210, and the cornea is treated similarly to an optical lens (mirror surface), so that the optical characteristic can be calculated. Here, the wavefront aberrations (corneal higher order aberrations) occurring at the front of the cornea are obtained (see FIG. 7(B)).

Next, the measurement part 111 of the arithmetic part 210 calculates output data, and stores the measurement results of the step S121 into the memory 240 (S122). As the output data, for example, data of the reference coordinate system, measurement data, an aberration amount itself of the subject eye, optical characteristic data, an ablation amount required for cutting by the surgical apparatus, and the like are obtained by performing an arithmetical operation.

Next, the arithmetic part 210 displays the measurement results and output data stored in the memory 240 at the step S122 on the display part 230 (S123). With respect to the display of the optical characteristic by the display part 240, for example, as shown in FIG. 7, the ocular higher order aberration map relating to the first measurement system and the corneal higher order aberration map relating to the second measurement system are separately displayed, and at the same time, (differential higher order aberration map)=(ocular higher order aberration map)−(corneal higher order aberration map)

is also displayed (see FIG. 7(C)). This differential higher order aberration map indicates the influence on the aberrations of the internal optical system except for the front of the cornea of the ocular optical system, and is a map very useful for diagnosis of such a disease that abnormality occurs in the refractive index distribution of a crystalline lens, for example, a cataract.

Further, as the needs arises, these output data can be outputted. Here, the form of the output includes, for example, modes as described below.

[1] The form which is an off-line mode and in which the output is made through a recording medium such as a floppy disk or a CD-ROM, or through an interface of a signal line, wireless line or the like, and then, a surgical operation is performed at a different timing.

[2] The form in which the output data is connected to the surgical apparatus 300 on-line through an interface of a signal line or the like, and at a surgical operation, the optical characteristic of the subject eye is measured continuously or by switching.

As described above, after the data output, if the measurement is not completed, it is repeated, and if completed, the measurement is ended (S125).

(2) Second Embodiment

Figure 17:
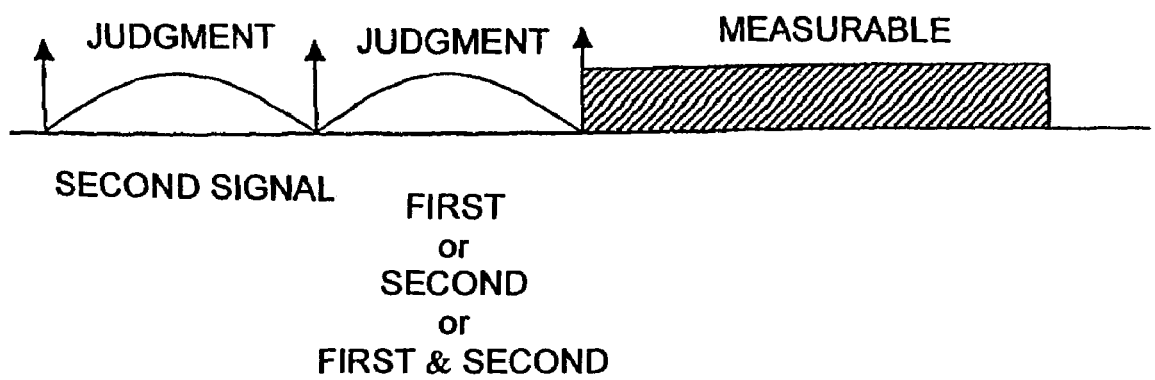
FIG. 17 is an explanatory view of a second embodiment of eye characteristic measurement.

FIG. 17 is an explanatory view of a second embodiment of eye characteristic measurement.

In this second embodiment, the measuring timing decision part 117 makes a first judgment as to the suitability of measurement in accordance with a first decision factor for measuring timing by, for example, the second signal, and after the judgment that the measurement can be performed is made, it further makes a second judgment as to the suitability of measurement in accordance with a second decision factor for measuring timing by the first signal and/or the second signal. When it is judged that the measurement can be performed by plural decision factors for measuring timing, a measurable range 91 is set, and the first and the second signals are captured. Incidentally, the first judgment by the first decision factor for measuring timing may be made with respect to the first signal or both the first and the second signals.

Figure 18:
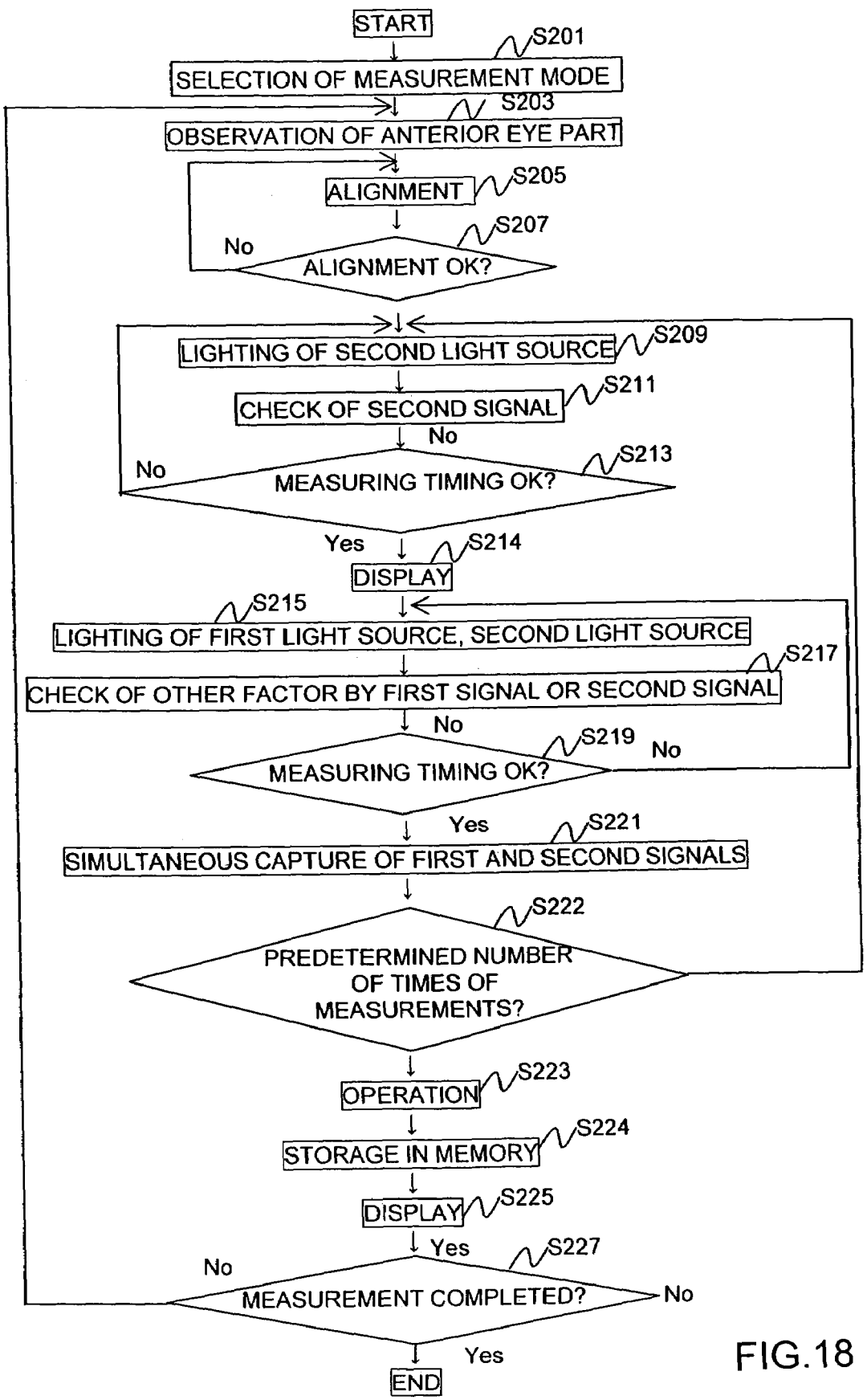
FIG. 18 is a flowchart of the second embodiment showing the operation of the eye optical characteristic measuring apparatus of the invention.

FIG. 18 is a flowchart of the second embodiment showing the operation of the eye characteristic measuring apparatus of the invention.

First, similarly to the first embodiment, respective processings of a measurement mode selection (S201), an anterior eye image measurement (S203), and alignments (S205, S207) are carried out.

Next, the optical characteristic measuring apparatus 100 switches on the second light source in accordance with the first decision factor for measuring timing set by the input part 270 (S209). In accordance with the first decision factor for measuring timing, the measuring timing decision part 117 of the arithmetic part 210 judges whether it is possible to set the measurable period 91 as the period of measuring timing (S213). When judging that the measurement can be performed in accordance with decision conditions corresponding to the respective decision factors for measuring timing, the measuring timing decision part 117 uses a lamp, a speaker or the like of the display part 230 to visually or audibly display that the measurement can be performed (S214).

Next, the optical characteristic measuring apparatus 100 switches on the first light source and/or the second light source in accordance with the second decision factor for measuring timing set by the input part 270 (S215). The measuring timing decision part 117 of the arithmetic part 210 judges whether setting of the measurable period 91 as the period of measuring timing can be performed in accordance with the second decision factor for measuring timing (S217). When the measuring timing decision part 117 judges that the measurement can be performed in accordance with decision conditions corresponding to the respective decision factors for measuring timing (S219), the measurement of the first and the second signals is performed in the respective modes selected at the step S101. In the case where the measurable period 91 can not be set at the step S219, a return to the step S215 is made again.

Next, similarly to the first embodiment, in accordance with the set mode, the arithmetic part 210 captures the first and the second signals simultaneously or substantially simultaneously (S221). Next, the arithmetic part 210 judges whether the measurement is performed a predetermined number of times or more to acquire the first and the second signals sufficient for measurement (S222). In the case where the measurement is not performed the predetermined number of times or more at the step S226, the arithmetic part 210 is again returned to the step S209. On the other hand, in the case where the measurement is performed the predetermined number of times or more at the step S222, the arithmetic part 210 performs an arithmetical operation on, for example, the optical characteristic of the eye 60 to be measured by the first signal, and further, performs an arithmetical operation on the corneal shape of the eye 60 to be measured by the second signal (S223). The arithmetic part 210 stores measurement results of the step S223 into the memory 240 (S224). The arithmetic part 210 displays the measurement results stored in the memory 240 at the step S224 on the display part 230 (S225). The arithmetic part 210 judges whether the measurements according to the respective processings are to be ended, and in the case where they are not to be ended, it is again returned to the step S203 (S227).

(3) Third Embodiment

Figure 19:
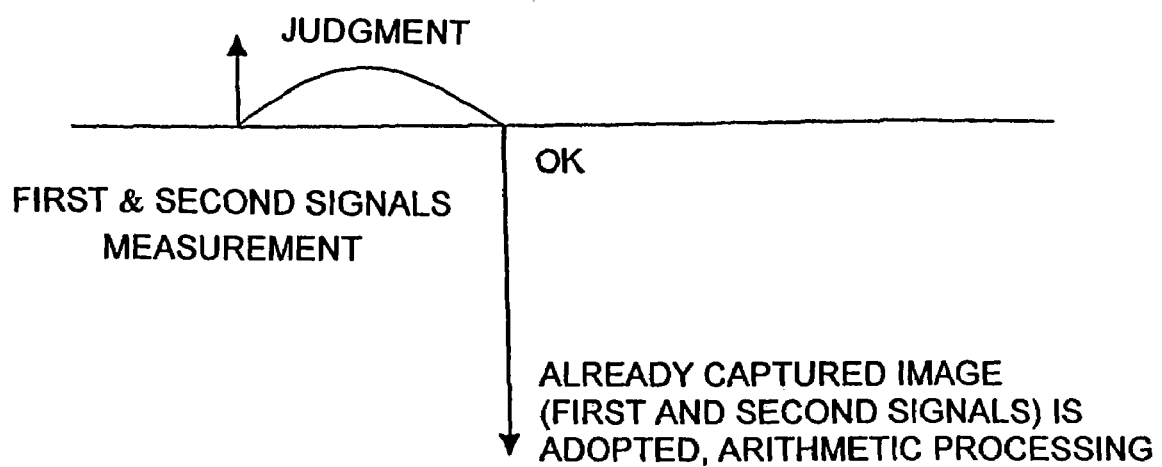
FIG. 19 is an explanatory view of a third embodiment of eye characteristic measurement.

FIG. 19 is an explanatory view of a third embodiment of eye characteristic measurement.

The third embodiment shows an operation of a case where for example, the first signal and the second signal are captured and then, it is judged whether the first signal and/or the second signal can be used as a measurement object signal. The measurement treatment signal decision part 118 of the arithmetic part 210 checks, for example, the first and the second signals captured simultaneously or substantially simultaneously. When the measurement object signal decision part 118 judges that a signal measured on the basis of one of or both of the signals can be used as the measurement object signal in accordance with the previously determined decision factor for measuring timing, it adopts both the signals and carries out a subsequent operation processing of an eye characteristic.

Figure 20:
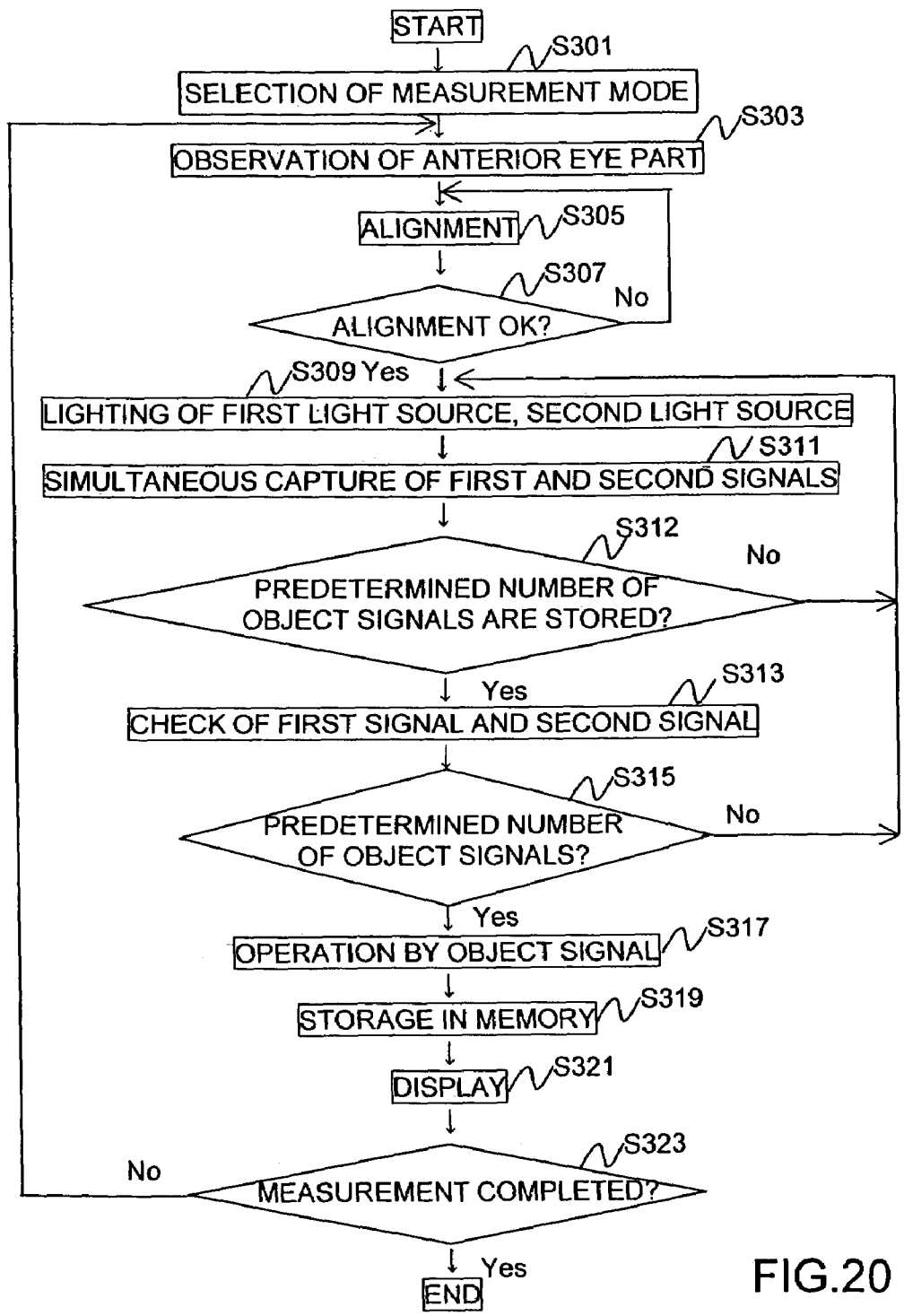
FIG. 20 is a flowchart of the third embodiment showing the operation of the eye optical characteristic measuring apparatus of the invention.

FIG. 20 is a flowchart of the third embodiment showing the operation of the eye optical characteristic measuring apparatus of the invention.

First, similarly to the first embodiment, respective processings of a measurement mode selection (S301), an anterior eye image measurement (S303), and alignments (S305, S307) are carried out.

Next, the optical characteristic measuring apparatus 100 switches on the first light source and the second light source (S309). In accordance with a selected mode, the arithmetic part 210 captures the first and the second signals simultaneously or substantially simultaneously (S311). Here, in an automatic mode, the arithmetic part 210 continuously captures both the signals by one or two or more at a suitable timing, and on the other hand, in a manual mode, it continuously captures both the signals by one or two or more by an operation measurement instruction. Next, the arithmetic part 210 judges whether with respect to the first and the second signals, a predetermined number of object signals sufficient for measurement are stored in the memory 240 (S312). The predetermined object signals are previously set by, for example, the input part 270 or the like. In the case where the predetermined number of object signals are not stored in the memory 240 at the step S312, the arithmetic part 210 is again returned to the step S309.

On the other hand, in the case where the predetermined number of object signals are stored in the memory 240 at the step S312, the measurement object signal decision part 118 of the arithmetic part 210 judges whether each pair of the captured first and second signals are suitable as the measuring object according to the decision factor for measuring timing previously set by, for example, the first signal and/or the second signal (S313). Here, the arithmetic part 210 judges whether there are a predetermined number of object signals with respect to the decision factor for the object signal acquired at the step S313 (S315), and is returned to the step S309 to repeat the above processing until the predetermined number of object signals are obtained. Next, the measurement object signal decision part 118 of the arithmetic part 210 adopts one or plural object signals previously determined by the input part 270 or the like among the object signals stored in the memory 240. Subsequently, similarly to the above embodiment, the arithmetic part 210 obtains the optical characteristic on the basis of the first and the second received light signals (S317). Next, the arithmetic part 210 calculates output data, stores them into the memory 240 (S319), displays them on the display part 230 (S321), and outputs these output data as the need arises.

Thereafter, if the measurement is not completed, the processing is repeated, and if completed, the measurement is ended (S323).

(4) Fourth Embodiment

Figure 21:
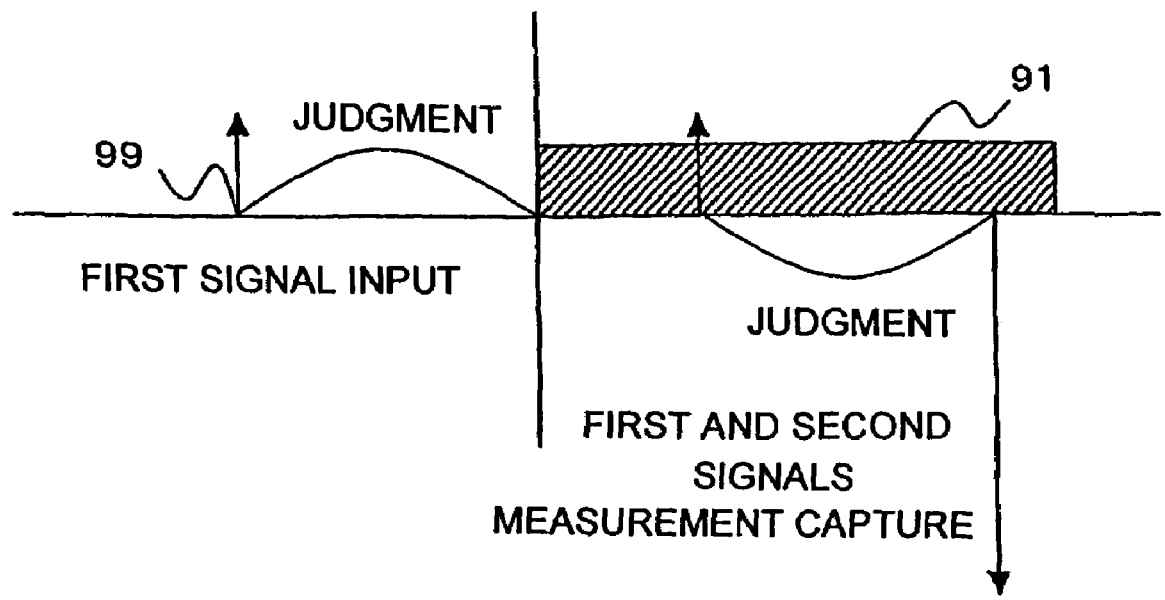
FIG. 21 is an explanatory view of a fourth embodiment of eye characteristic measurement.

FIG. 21 is an explanatory view of a fourth embodiment of eye characteristic measurement.

This fourth embodiment shows an operation in a case where for example, a measuring timing is decided by the first signal, and after the first signal and the second signal are captured, a measurement object signal is decided. The measuring timing decision part 117 of the arithmetic part 210 first receives the first signal, and checks in accordance with the decision factor for measuring timing. Incidentally, this check may be performed by the second signal or both the signals. When the measuring timing decision part 117 judges that a measurable period occurs, the measurement object signal decision part 118 of the arithmetic part 210 captures the first signal and the second signal in the measurable period 91 simultaneously or substantially simultaneously, and performs the measurement check of the first and the second signals. When judging that the signal measured on the basis of one of or both of the signals can be used as the measurement object signal in accordance with the previously determined decision factor for measuring timing, the measurement object signal decision part 118 adopts both the signals, and carries out a subsequent operation processing of an eye characteristic.

Figure 22:
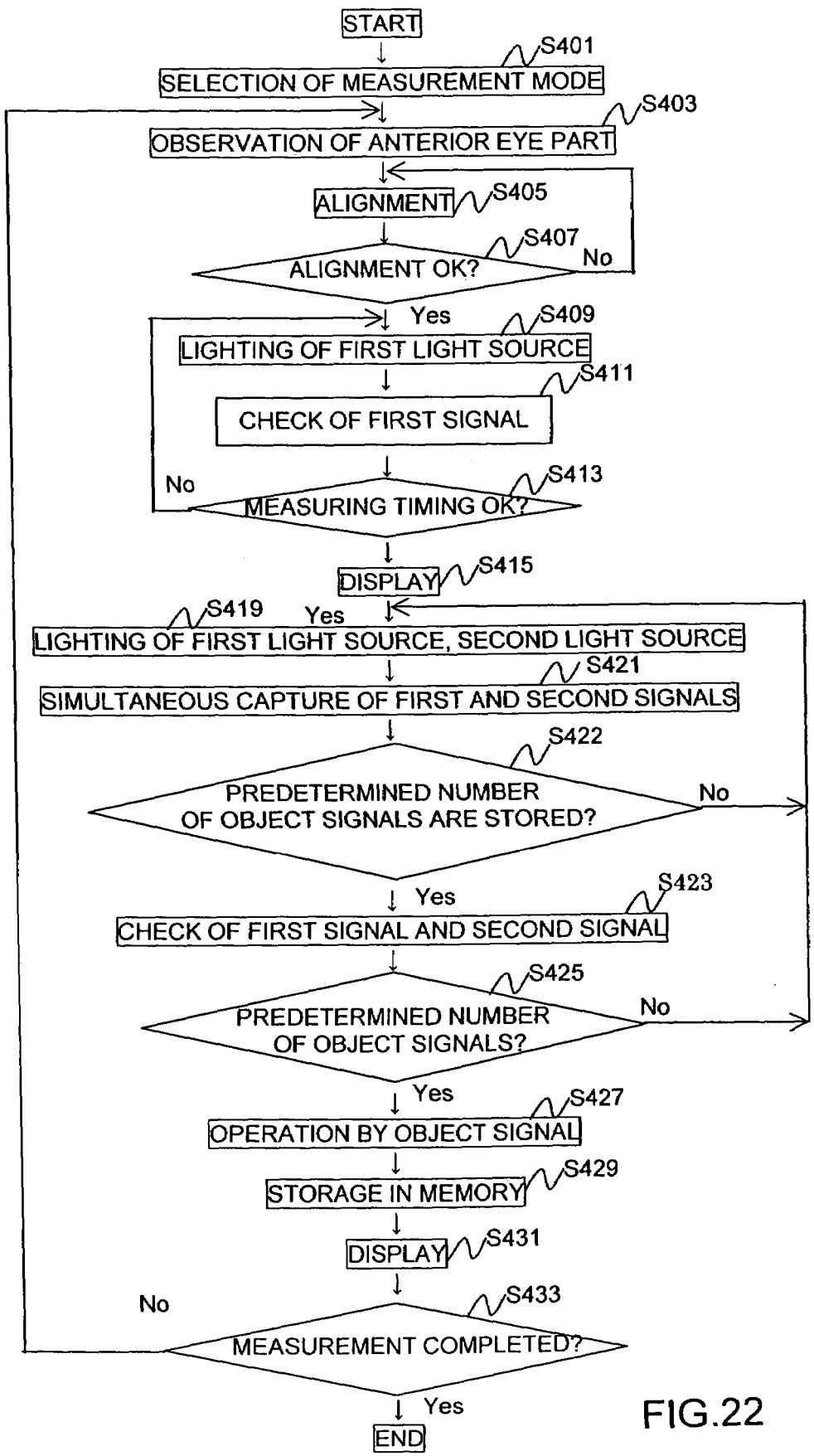
FIG. 22 is a flowchart of the fourth embodiment showing the operation of the eye optical characteristic measuring apparatus of the invention.

FIG. 22 is a flowchart of the fourth embodiment showing the operation of the eye optical characteristic measuring apparatus of the invention.

First, similarly to the first embodiment, respective processings of a measurement mode selection (S401), an anterior eye image measurement (S403), and alignments (S405, S407) are carried out.

Next, the optical characteristic measuring apparatus 100 switches on the first light source in accordance with a first decision factor for measuring timing set by the input part 270 (S409). In accordance with the decision factor for measuring timing, the measuring timing decision part 117 of the arithmetic part 210 judges whether setting of the measurable period 91 as the period of the measuring timing can be performed (S411). When judging that the measurement can be performed in accordance with decision conditions corresponding to the respective decision factors for measuring timing (S413), the measuring timing decision part 117 visually or audibly displays that the measurement can be performed by the display part 230 or the like (S415).

Next, similarly to the third embodiment, the optical characteristic measuring apparatus 100 switches on the first light source and the second light source (S419). In accordance with the mode set by the input part 270, the arithmetic part 210 captures the first and the second signals simultaneously or substantially simultaneously (S421), and judges whether with respect to the first and the second signals, a predetermined number of object signals sufficient for measurement are stored in the memory 240 (S422). In the case where the predetermined number of object signals are not stored in the memory 240 at the step S422, the arithmetic part 210 is again returned to the step S419.

On the other hand, in the case where the predetermined number of object signals are stored in the memory 240 at the step S422, the measurement object signal decision part 118 of the arithmetic part 210 judges whether each pair of the captured first and second signals are suitable as the measuring object according to the decision factor for measuring timing previously set by, for example, the first signal and/or the second signal (S423). Here, the arithmetic part 210 judges whether there are a predetermined number of object signals with respect to the decision factor for the object signal acquired at the step S423 (S425), and is returned to the step S419 to repeat the foregoing processing until the predetermined number of object signals are obtained. The measurement object signal decision part 118 of the arithmetic part 210 adopts one or plural object signals previously determined by the input part 270 or the like among the object signals stored in the memory 240. Subsequently, similarly to the foregoing embodiment, the arithmetic part 210 obtains the optical characteristic on the basis of the first and the second received light signals (S427). Next, the arithmetic part 210 calculates output data, stores them into the memory 240 (S429), displays them on the display part 230 (S431), and outputs these output data as the need arises. Thereafter, if the measurement is not completed, the processing is repeated, and if completed, the measurement is ended (S433).

INDUSTRIAL APPLICABILITY

According to the invention, as described above, it is possible to provide the eye optical characteristic measuring apparatus which correlates the aberrations of the subject eye or the refractive power data obtained from the first light receiving part with the corneal data of the subject eye obtained from the second light receiving part so that they can be precisely superimposed. Besides, according to the invention, pupils of both are visually compared to make positions coincide with each other, so that coordinates of the corneal shape measurement using the same image as the alignment system and those of the wavefront measurement can be made to coincide with each other.

Further, according to the invention, as described above, it is possible to provide the eye characteristic measuring apparatus which captures the first signal and the second signal simultaneously, and can simultaneously measure the optical characteristic of the subject eye and the corneal shape. Besides, according to the invention, the first signal and the second signal can be captured simultaneously or continuously. Besides, according to the invention, in consideration of the influence of the state of the first signal and the second signal on the measurement, the measurement can be performed when the states of the first signal and the second signal become such states where highly reliable measurement results can be obtained.

Besides, according to the invention, the suitability of plural factors having influence on measurement is judged, and the suitable measuring timing can be decided. Besides, according to the invention, the first signal and the second signal can be simultaneously captured plural times continuously. Besides, according to the invention, the timing when the first signal and the second signal suitable for measurement are captured can be decided.

The invention claimed is:

1. An eye characteristic measuring apparatus comprising:
a first illuminating optical system including a first light source part for emitting a first light flux of a first wavelength, for illuminating a retina of a subject eye to be measured with the first light flux from the first light source part;
a first light receiving optical system including a first light receiving part for forming a first received light signal as a first coordinate system from a received light flux, and a conversion member converting the light flux reflected and returned from the retina of the subject eye into plural beams and guiding them to the first light receiving part, wherein the conversion member and the pupil of the subject eye form a conjugated relation;

a second light receiving optical system including a second light receiving part for forming a second received light signal, as a second coordinate system, including information of an anterior eye part from a received light flux, for guiding a second light flux including the information of the anterior eye part of the subject eye to the second light receiving part;

a measurement part for obtaining a first optical characteristic of the subject eye on the basis of the first received light signal from the first light receiving part and a second optical characteristic of the subject eye on the basis of the second received light signal from the second light receiving part;

a coordinate setting part for converting signals of the first and the second coordinate systems corresponding to a pupil of the subject eye included in the first and the second received light signals into signals of reference coordinate systems, respectively; and a conversion part for correlating, through the respective reference coordinate systems formed by the coordinate setting part, the first and the second optical characteristics of the subject eye obtained by the measurement part.

2. The eye characteristic measuring apparatus as set forth in claim 1, wherein the coordinate setting part decides an origin of coordinates on the basis of a background light appearing to surround the beams converted by the conversion member on the first light receiving part.

3. The eye characteristic measuring apparatus as set forth in claim 2, wherein the coordinate setting part decides a barycenter of the contour as the origin of the coordinates, on the basis of a contour of the background light appearing to surround the beams converted by the conversion member on the first light receiving part.

4. The eye characteristic measuring apparatus as set forth in claim 1, wherein the coordinate setting part decides an origin of coordinates and a direction of a coordinate axis, on the basis of the second received light signal including a feature portion of the subject eye.

5. The eye characteristic measuring apparatus as set forth in claim 4, wherein the feature portion of the subject eye includes at least one of a subject eye pupil position of the subject eye, an iris position of the subject eye, a pupil shape, a limbus shape, an iris pattern of the subject eye, and a marker formed on an anterior eye part of the subject eye.

6. The eye characteristic measuring apparatus as set forth in claim 1, wherein the coordinate setting part decides an origin of coordinates as a pupil center or a corneal vertex, on the basis of the second received light signal including a feature portion of the subject eye.

7. The eye characteristic measuring apparatus as set forth in claim 1, wherein the coordinate setting part obtains an origin of coordinates on the basis of at least one of, in the second received light signal, a pupil position of the subject eye, an iris position of the subject eye, a pupil shape, a limbus shape, and an iris pattern of the subject eye, obtains rotation and movement of a coordinate axis on the basis of at least one of, in the second received light signal, a pupil position of the subject eye, an iris position of the subject eye, a pupil shape, a limbus shape, and an iris pattern of the subject eye, and correlates measurement data with the coordinate axis.

8. The eye characteristic measuring apparatus as set forth in claim 1, further comprising an arithmetic part for performing an arithmetical operation on an ablation amount on the basis of the aberrations result and outputting a result of the operation to a surgical apparatus.

9. The eye characteristic measuring apparatus as set forth in claim 1, further comprising a marker formation part for forming, on the basis of the reference coordinate system set by the coordinate setting part, a marker correlated with the coordinate system on the anterior eye part of the subject eye.

10. The eye characteristic measuring apparatus as set forth in claim 1, wherein the coordinate setting part obtains a pupil edge and a pupil center on the basis of the respective signals of the first and the second coordinate systems.

11. The eye characteristic measuring apparatus as set forth in claim 1, wherein the conversion part performs conversion into the reference coordinate system by making a pupil center obtained by the coordinate setting part an origin.

12. An eye characteristic measuring apparatus comprising:

a first illuminating optical system including a first light source part for emitting a first light flux of a first wavelength, for illuminating a retina of a subject eye to be measured with the first light flux from the first light source part;

a first light receiving optical system including a first light receiving part for forming a first received light signal as a first coordinate system from a received light flux, and a conversion member converting the light flux reflected and returned from the retina of the subject eye into plural beams and guiding them to the first light receiving part, wherein the conversion member and the pupil of the subject eye form a conjugated relation;

a second light receiving optical system including a second light receiving part for forming a second received light signal, as a second coordinate system, including information of an anterior eye part from a received light flux, for guiding a second light flux including the information of the anterior eye part of the subject eye to the second light receiving part;

a measurement part for obtaining a first optical characteristic of the subject eye on the basis of the first received light signal from the first light receiving part;

a coordinate setting part for converting signals of the first and the second coordinate systems corresponding to a pupil of the subject eye included in the first and the second received light signals into signals of reference coordinate systems, respectively; and a conversion part for correlating, through the respective reference coordinate systems formed by the coordinate setting part, the first optical characteristic of the subject eye obtained by the measurement part.

13. An eye characteristic measuring apparatus comprising:

a first light source part for emitting a first light flux of a near-infrared first wavelength;

a first illuminating optical system for illuminating a minute region on a retina of a subject eye with the light flux from the first light source part;

a first light receiving optical system for receiving a light through a first conversion member for converting a part of a first reflected light flux, which is originated from the first light flux from the first light source part and is reflected from the retina of the subject eye, into substantially at least 17 beams;

a first light receiving part for receiving a first received light flux guided by the first light receiving optical system to form a first signal;

a second light source part for emitting a second flux of a near-infrared second wavelength longer than the first wavelength of the first light flux;

a second illuminating optical system for illuminating a vicinity of a cornea of the subject eye with the second light flux from the second light source and with a specified pattern;

a second light receiving optical system for receiving a second reflected light flux which is originated from the second light flux from the second light source part and is reflected from the vicinity of the cornea of the subject eye;

a second light receiving part for receiving a second received light flux guided by the second light receiving optical system to form a second signal; and an arithmetic part for capturing the first and the second signals from the first light receiving part and the second light receiving part at a same or substantially same timing, obtaining an optical characteristic of the subject eye on the basis of the first signal from the first light receiving part, and obtaining a corneal shape of the subject eye on the basis of the second signal from the second light receiving part.

14. The eye characteristic measuring apparatus as set forth in claim 13, further comprising a measuring timing decision part for deciding, on the basis of the first and/or the second signal, measuring timings of the first signal and the second signal as an object on which a measurement operation is performed.

15. The eye characteristic measuring apparatus as set forth in claim 14, wherein the measuring timing decision part uses, as a specified decision factor for measuring timing, at least one of a blink of the subject eye, a poor tear film, a lack of a pupil diameter and a poor opening eyelid.

16. The eye characteristic measuring apparatus as set forth in claim 15, wherein the measuring timing decision part judges suitability according to a first decision factor for measuring timing on the basis of the first signal, judges suitability according to a second decision factor for measuring timing on the basis of the second signal, and decides the measuring timings of the first signal and the second signal according to these judgments.

17. The eye characteristic measuring apparatus as set forth in claim 16, wherein
the first decision factor for measuring timing is at least one of the blink of the subject eye, the poor tear film, the lack of the pupil diameter, and the poor opening eyelid, and
the second decision factor for measuring timing is at least one of the blink of the subject eye, the poor tear film, the lack of the pupil diameter, the poor opening eyelid, and a fixation disparity.

18. The eye characteristic measuring apparatus as set forth in claim 17, wherein the measuring timing decision part detects the blink of the subject eye on the basis of the first signal and/or the second signal, sets a specified measurable range on the basis of a timing of the blink, and decides the measuring timings of the first signal and the second signal on the basis of the suitability according to the decision factor for measuring timing of the first signal or the second signal.

19. The eye characteristic measuring apparatus as set forth in claim 18, wherein as the decision factor for measuring timing concerning the first signal or the second signal, at least one of a pupil diameter, a state of the tear film, and an eyelid opening degree is selectively set.

20. The eye characteristic measuring apparatus as set forth in claim 13, wherein the measuring timing decision part decides the measuring timings of the first signal and the second signal at a same timing.

21. The eye characteristic measuring apparatus as set forth in claim 13, wherein the arithmetic part further comprises a measurement object signal decision part for determining the first signal and the second signal as an object on which a measurement operation is performed.

22. The eye characteristic measuring apparatus as set forth claim 21, wherein the measurement object signal decision part judges suitability according to a specified decision factor for measuring timing on the basis of the first signal and/or the second signal, and decides measurement object signals of the first signal and the second signal.

23. The eye characteristic measuring apparatus as set forth claim 22, wherein the specified decision factor for the measurement object signal is at least one of a blink of the subject eye, a poor tear film, a lack of a pupil diameter, and a poor opening eyelid.

24. The eye characteristic measuring apparatus as set forth claim 23, wherein the measurement object signal decision part judges suitability according to a first decision factor for measuring timing on the basis of the first signal, judges suitability according to a second decision factor for measuring timing on the basis of the second signal, and decides the measuring timings of the first signal and the second signal according to these judgments.

25. The eye characteristic measuring apparatus as set forth in claim 24, wherein
the first decision factor for measuring timing is at least one of the blink of the subject eye, the poor tear film, the lack of the pupil diameter, and the poor opening eyelid, and
the second decision factor for measuring timing is at least one of the blink of the subject eye, the poor tear film, the lack of the pupil diameter, the poor opening eyelid, and a fixation disparity.

26. The eye characteristic measuring apparatus as set forth in claim 13, wherein the arithmetic part obtains an optical characteristic of the subject eye on the basis of the first signal captured plural times, and obtains a corneal shape of the subject eye on the basis of the second signal captured plural times from the second light receiving part at a same or substantially same timing.

27. The eye characteristic measuring apparatus as set forth in claim 13, wherein the first light source is formed of a super luminescence diode, and the second light source is formed of a light emitting diode.

28. The eye characteristic measuring apparatus as set forth in claim 13, wherein the first wavelength is 840 nm, and the second wavelength is 940 nm.

29. The eye characteristic measuring apparatus as set forth in claim 13, wherein when measurement fitting conditions of the first signal and the second signal are fulfilled, a measurement is automatically started, or the measurement is permitted.

30. The eye characteristic measuring apparatus as set forth in claim 13, further comprising:
a third illuminating optical system for illuminating a cornea of the subject eye with a parallel light flux; and
a visual line detection part for detecting a visual line direction of the subject eye on the basis of a position of an illuminating light by the third illuminating optical system from the second light receiving part, wherein
the arithmetic part suppresses a measurement when the visual line detection part detects a fixation disparity.

31. The eye characteristic measuring apparatus as set forth in claim 13, wherein the arithmetic part can select a continuous measurement mode, and in the continuous measurement mode, in a case where a measurement fitting condition of the first signal or the second signal is fulfilled, measurements of the first signal and the second signal are performed at specified intervals.

32. The eye characteristic measuring apparatus as set forth in claim 13, wherein the arithmetic part can select a continuous measurement mode, and in the continuous measurement mode, in a case where the measurement fitting condition of the first signal or the second signal is again fulfilled, a measurement is automatically performed.

33. The eye characteristic measuring apparatus as set forth in claim 13, wherein the arithmetic part can select a learning mode, and in a case where the learning mode is selected, a measurement fitting condition at a measurement thereof is stored, and is made to be reflected in setting of a measurement fitting condition of the first signal or the second signal.

34. The eye characteristic measuring apparatus as set forth in claim 13, wherein the arithmetic part stores a signal of the second light receiving part when a measurement is performed, and the signal of the second light receiving part, together with measurement data, can be displayed on a display part.

35. The eye characteristic measuring apparatus as set forth in claim 13, wherein the measuring timing decision part further receives a signal corresponding to a pulse of a person to be measured, and in accordance with the signal corresponding to the pulse, decides a subsequent measuring timing in a substantially same state as a pulse state at a timing point of an initial measurement.

36. The eye characteristic measuring apparatus as set forth in claim 13, wherein the measuring timing decision part further receives a signal corresponding to a pulse of a person to be measured, and in accordance with the signal corresponding to the pulse, decides a measuring timing when a specified pulse state occurs.

* * * * *